United States Patent
Morimura et al.

(10) Patent No.: US 10,541,807 B1
(45) Date of Patent: Jan. 21, 2020

(54) SYSTEM AND METHOD FOR HEALTHCARE SECURITY AND INTEROPERABILITY

(71) Applicant: Janssen Pharmaceutica NV, Beerse (BE)

(72) Inventors: Jun Morimura, Princeton, NJ (US); Jessica Lee, Edison, NJ (US); Rama Kondru, Morris Plains, NJ (US); Thomas Doyle, Hoboken, NJ (US); Lichen Shen, Irvine, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/251,980

(22) Filed: Jan. 18, 2019

(51) Int. Cl.
  *H04L 9/06* (2006.01)
  *G16H 10/60* (2018.01)
  *G16H 15/00* (2018.01)

(52) U.S. Cl.
  CPC .......... *H04L 9/0618* (2013.01); *G16H 10/60* (2018.01); *G16H 15/00* (2018.01); *H04L 2209/38* (2013.01)

(58) Field of Classification Search
  CPC ... H04L 9/0618; H04L 2209/38; G16H 15/00; G16H 10/60
  See application file for complete search history.

(56) References Cited

U.S. PATENT DOCUMENTS

| | | | |
|---|---|---|---|
| 2017/0091397 A1* | 3/2017 | Shah | H04L 9/3236 |
| 2018/0060496 A1* | 3/2018 | Bulleit | G16H 10/60 |
| 2018/0103042 A1* | 4/2018 | Castagna | H04L 63/08 |
| 2018/0165588 A1* | 6/2018 | Saxena | G06F 19/324 |
| 2018/0198624 A1* | 7/2018 | Bisti | H04L 9/3247 |
| 2018/0253464 A1* | 9/2018 | Kohli | H04L 9/3236 |
| 2018/0343110 A1* | 11/2018 | Funk | H04L 9/0618 |

* cited by examiner

*Primary Examiner* — Huan V Doan
(74) *Attorney, Agent, or Firm* — Venkatesh Krishnamoorthy; Silicon Valley Patent Group, LLP

(57) ABSTRACT

Disclosed embodiments facilitate healthcare system security and interoperability. In some embodiments, a first entity may receive, in response to a transaction at a first time, encrypted information blocks pertaining to the transaction from one or more second entities. Each encrypted information block may be received from a distinct second entity and may comprise at least one sub-block decryptable by the first entity. The first entity may decrypt the decryptable sub-blocks and augment a multi-dimensional blockchain. The multi-dimensional blockchain may be augmented with a multi-dimensional block formed by linking at least one of the encrypted information blocks received from the one or more second entities to a current block being added to a blockchain associated with the transaction and maintained by the first entity. The first entity may then enable access to the multi-dimensional blockchain for at least one of the one or more second entities.

25 Claims, 13 Drawing Sheets

SYSTEM AND METHOD FOR HEALTHCARE SECURITY AND INTEROPERABILITY

FIELD

The subject matter disclosed herein relates to healthcare system security and healthcare system interoperability.

BACKGROUND

Healthcare information systems face compliance challenges that limit interoperability. For example, stored information may be subject to various privacy regulations such as Health Insurance Portability and Accountability Act (HIPAA). Privacy rules under HIPAAA establish national standards to protect individual medical records and other personal health information when health care transactions are conducted electronically. These regulations may cover privacy (e.g. which entities have access to information), content (what information an authorized entity may access), security (how the information is protected from unauthorized access when stored and during electronic communication) and integrity (the accuracy and authenticity of information). In addition, commercially valuable information may be protected under an organizational policy that may limit sharing of the information with third parties (e.g. as trade secrets, and/or for business or commercial reasons). Regulations such as the European Union (EU) General Data Protection Regulation (GDPR) may also impact information collection, storage, sharing, and communication. These regulations have affected the information available to healthcare marketplace participants and led to the creation of organizational "data silos," where information available to an entity is isolated, even when it could be useful systemically (e.g. to another non-competitive entity). Such compartmentalization of information has led to increased systemic costs (e.g. by a medical provider considering the costs of treatment alternatives), raised patient risk (e.g. from drug interactions, prescription abuse etc.), and limiting the efficacy of outcome based approaches to medical treatment or remediation (e.g. making it more difficult and expensive to determine when a desired outcome has been achieved or compare metrics in approaches that achieve similar outcomes). Approaches to address one or more of the above issues that would help facilitate healthcare information security while promoting interoperability between marketplace participants are therefore desirable.

SUMMARY

In some embodiments, a processor-implemented method may comprise: receiving, at a first entity in response to a transaction at a first time, encrypted information blocks pertaining to the transaction from one or more second entities, wherein each encrypted information block is received from a distinct second entity and comprises at least one sub-block decryptable by the first entity; decrypting, by the first entity, the decryptable sub-blocks; augmenting, by the first entity, a multi-dimensional blockchain, wherein the multi-dimensional blockchain is augmented with a multi-dimensional block formed by linking at least one of the encrypted information blocks received from the one or more second entities to a current block being added to a blockchain associated with the transaction and maintained by the first entity; and enabling access to the multi-dimensional blockchain for at least one of the one or more second entities.

In another aspect, a server for a first entity may comprise: a memory, a communications interface, and a processor coupled to the memory and the communications interface. In some embodiments, the processor may be configured to: receive, over the communications interface, at the first entity in response to a transaction at a first time, encrypted information blocks pertaining to the transaction from one or more second entities, wherein each encrypted information block is received from a distinct second entity and comprises at least one sub-block decryptable by the first entity; decrypt, by the first entity, the decryptable sub-blocks; augment, by the first entity, a multi-dimensional blockchain resident in the memory, wherein the multi-dimensional blockchain is augmented with a multi-dimensional block formed by linking at least one of the encrypted information blocks received from the one or more second entities to a current block being added to a blockchain associated with the transaction and maintained by the first entity; and enable access to the multi-dimensional blockchain by at least one of the one or more second entities.

In a further aspect, an apparatus may comprise: means for receiving, at a first entity in response to a transaction at a first time, encrypted information blocks pertaining to the transaction from one or more second entities, wherein each encrypted information block is received from a distinct second entity and comprises at least one sub-block decryptable by the first entity; means for decrypting, by the first entity, the decryptable sub-blocks; means for augmenting, by the first entity, a multi-dimensional blockchain, wherein the multi-dimensional blockchain is augmented with a multi-dimensional block formed by linking at least one of the encrypted information blocks received from the one or more second entities to a current block being added to a blockchain associated with the transaction and maintained by the first entity; and means for enabling access to the multi-dimensional blockchain for at least one of the one or more second entities.

In some embodiments, a non-transitory computer-readable medium may comprise executable instructions to configure a processor to: receive, over the communications interface, at the first entity in response to a transaction at a first time, encrypted information blocks pertaining to the transaction from one or more second entities, wherein each encrypted information block is received from a distinct second entity and comprises at least one sub-block decryptable by the first entity; decrypt, by the first entity, the decryptable sub-blocks; augment, by the first entity, a multi-dimensional blockchain resident in the memory, wherein the multi-dimensional blockchain is augmented with a multi-dimensional block formed by linking at least one of the encrypted information blocks received from the one or more second entities to a current block being added to a blockchain associated with the transaction and maintained by the first entity; and enable access to the multi-dimensional blockchain by at least one of the one or more second entities.

The methods disclosed may be performed by one or more computers, including servers, cloud-based systems, etc. using computer-readable media or computer-readable memory.

BRIEF DESCRIPTION OF THE DRAWINGS

Embodiments of the invention will be described, by way of example only, with reference to the drawings.

DETAILED DESCRIPTION

Disclosed embodiments facilitate healthcare system security while promoting healthcare system integrity and interoperability.

Figure 1A:
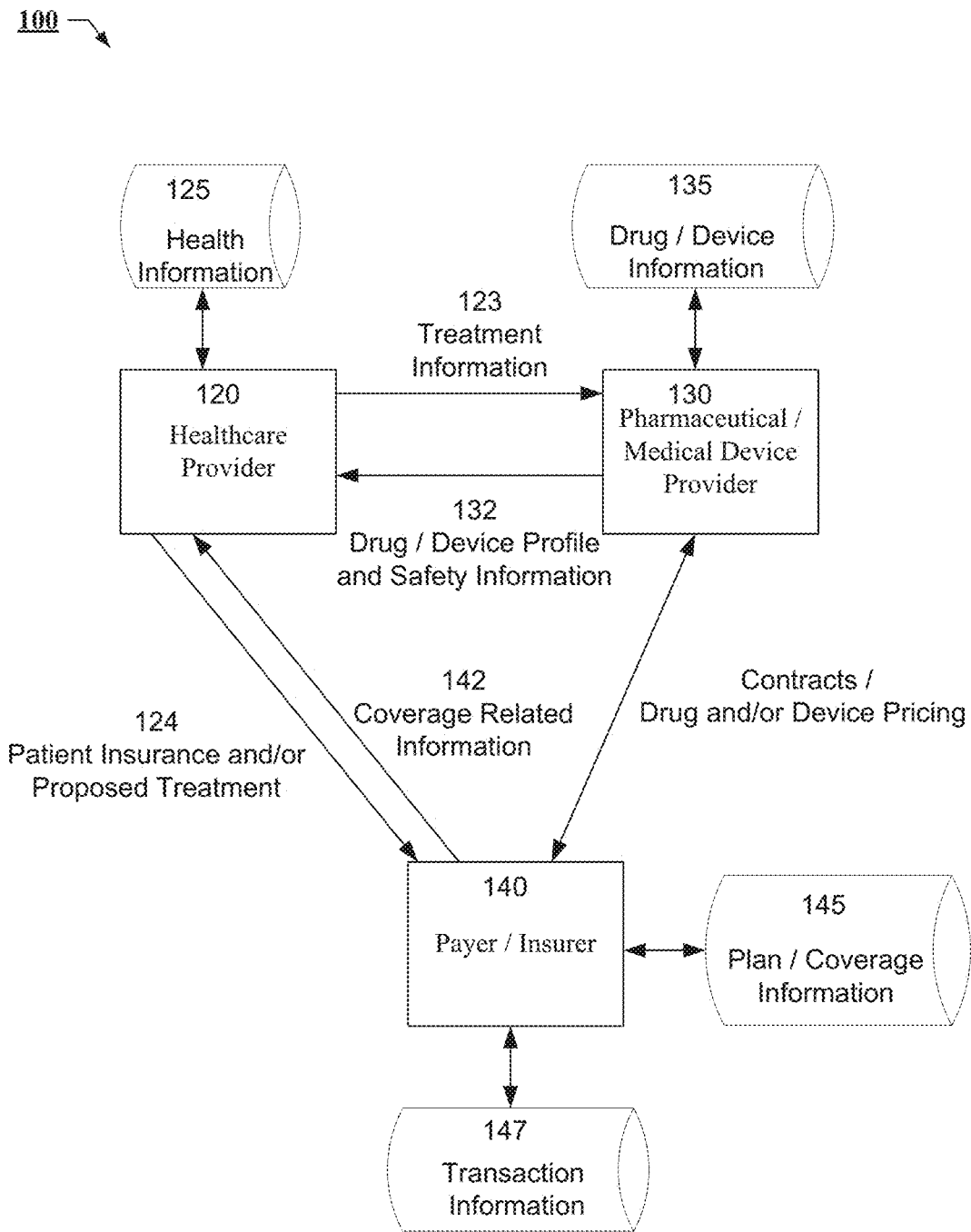
FIG. 1A shows a schematic block diagram illustrating conventional healthcare information system operation.

FIG. 1A shows a schematic block diagram illustrating the operation of a conventional healthcare information system 100. Healthcare transactions may involve several entities, where each entity may have some information relevant to the transaction, which may be used to complete the transaction. Thus, in conventional systems, some limited information may be exchanged between the transacting entities in order to complete a transaction. The term "entity," as used herein, may refer to an individual (such as a patient or groups of patients) or an organization or that participates in a healthcare marketplace and/or computing and information systems (e.g. hardware and/or software) associated with that individual/group/organization, which may participate in the healthcare marketplace on the individual/group/organization's behalf. For example, the computing systems associated with one entity may process and/or exchange information with computing systems associated with other entities. The exchange of information between entities may occur over secure communication networks and/or in a secure manner (e.g. using encryption) over the Internet.

An entity such as a patient (not shown in FIG. 1) may seek treatment from another entity such as Healthcare Provider (HCP) 120 for a medical condition afflicting the patient. Based on health information 125 of the patient, which may be maintained by HCP 120 (or obtained by HCP 120 from the patient), HCP 120 may determine patient insurance and treatment information 124. As shown in FIG. 1, HCP 120 may send patient insurance and treatment information 124 to Payer/Insurer (hereinafter "Payer") 140. Insurance related and treatment information 124 may include patient identification (ID) information, insurance plan information, group ID information proposed treatment, etc. However, patient insurance and treatment information 124 may not include patient family history and/or other patient information, which may not be relevant to coverage and/or cost determination, and/or may be prevented (e.g. by regulations) from being shared with Payer 140.

Payer 140 may compare the received insurance related information 124 with information in Plan/Coverage database 145 to determine coverage for the patient. Based on the coverage information, Payer 140 may update transaction information database 147 and provide patient coverage related information 142 to HCP 120. Coverage related information may include approval/denial information, coverage information related to the proposed treatment, and cost and payment related information such as patient co-pays, billing codes, etc. If the Payer withholds approval or the coverage for the proposed treatment is inadequate and/or does not meet the patient's cost criteria, HCP may propose revisions, which may lead to further exchange of information between HCP 120 and Payer 140.

In addition, when proposing a treatment is prescribed, HCP 120 may also send treatment information 123 to Pharmaceutical Provider and/or Medical Device Provider (PMDP) 130. Treatment information 123 may include information related to medical conditions afflicting the patient, other medication being used by the patient. However, treatment information 123 may not include any personally identifiable information (PII) related to the patient. In response, PMDP 130 may send Drug/Device profile and safety information 132 to HCP 120. Drug/Device profile and safety information may include information about drug characteristics such as dosage, mode of administration, absorption, metabolism, duration of action, toxicity, and interactions with foods or other medications. Upon receiving Drug/Device profile and safety information 132, HCP may prescribe the drug and/or medical device, or may revise the prescription based on the Drug/Device profile and safety information 132. The interactions between HCP 120, Payer 140, and PMDP 130 may continue until HCP 120 finalizes a treatment plan that: (a) is acceptable to the patient, (b) meets safety and efficacy considerations, and (c) may be covered and/or approved by Payer 140.

Thus, conventional healthcare information systems suffer from several drawbacks. While each entity obtains and maintains information that may be relevant for operating its business, very little of that information is shared (e.g. due to legal, privacy, and/or business considerations) and when information is shared, it is often piecemeal, devoid of context and may not be useful. For example, HCP 120 may not provide details of adverse drug effects to PMDP 130. As another example, when adverse drug effect information is provided to PMDP 130 by HCP 120, the information may not include non-PII demographic information (e.g. age, location, medical condition, etc. for a patient) so the information may be of limited value to PMDP 130. In addition, in some instances, when adverse drug effects are reported by an entity (e.g. a patient), the adverse drug effects may be validated by another entity (e.g. HCP 120) to determine if the adverse event can be attributed to a prescribed drug. Validation, which may involve additional entities, can introduce additional complexities that can further delay reporting and/or create additional silos thereby further limiting the utility of the information (e.g. to PMDP 130).

In addition, because the information is compartmentalized and may be provided on an ad-hoc basis, aggregating the received information with information stored by the receiving entity may be cumbersome. Moreover, because each entity may index the information differently, it may be difficult or impossible for the receiving entity (or the sending entity) to tie received (or sent) information to an information record (e.g. stored by the sending entity), where the transmitted information originated. For example, if HCP 120 provides adverse drug effect information to a PMDP 130 at some point in time, it may be difficult for HCP 120 and/or PMDP 130 to obtain additional patient or patient medical condition information pertaining to the adverse drug effect—even when that information may be legally shared. For example, compartmentalization of information may prevent or limit access by PMDP 130 to aggregate demographic information that may be of use in tailoring drug utilization. As another example, the costs of various treatment alternatives may not be available to the patient or HCP 120 at the time when a prescription or treatment plan is being developed. As a further example, it may be difficult for HCPs 120 and/or Payer's 140 to determine prescription abuse by patients.

Many modern machine learning (ML) and other artificial intelligence (AI) systems can process large amounts of data to determine hazards, identify patterns that may lead to desired outcomes, etc., which may lead to increased efficiencies, lower costs, and/or better outcomes. The siloing and compartmentalization of information also limits the applicability of such ML and AI techniques thereby contributing to inefficiencies.

Some attempts to introduce efficiencies into healthcare delivery focus on outcome based approaches. Payers 140 may tie reimbursement to the achievement of some agreed upon outcomes. For example, an outcome based contract may specify that HCP 120 will be reimbursed at some agreed upon rate based on a lowering of a patient's blood pressure to some defined range within some time period. Tracking and managing such outcome based contracts can be notoriously difficult in conventional systems because several exchanges of information may need to occur between HCP 120 and Payer 140 where each exchange is in compliance with legal, regulatory, privacy and business related guidelines.

Figure 1B:
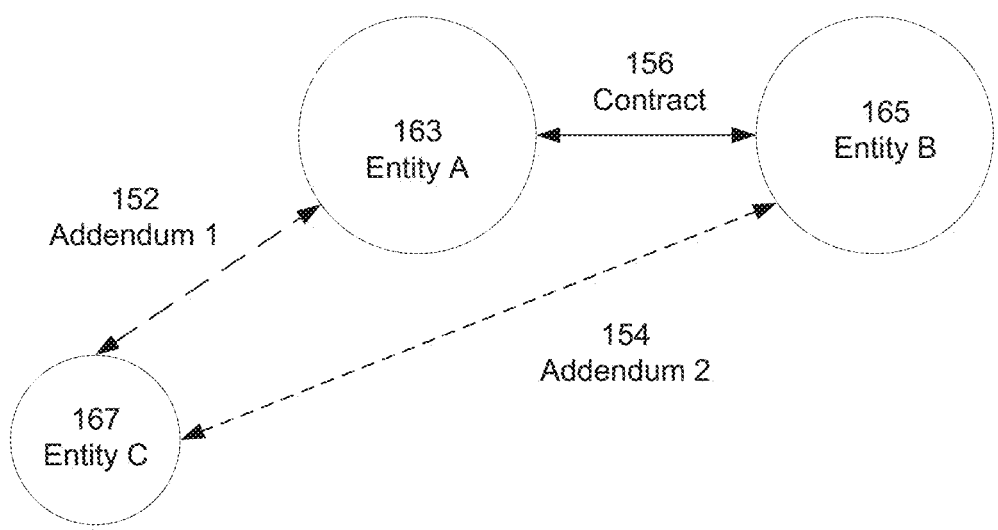
FIG. 1B shows conventional implementation of contracts associated with a traditional blockchain system.

FIG. 1B shows conventional implementation of contracts associated with a traditional blockchain system. As shown in FIG. 1B, program code may implement a contract 156 between entity A 163 and entity B 165. In a conventional system, information may be exchanged (e.g. as outlined above in relation to FIG. 1A) between entity A 163 and entity B 165 separately, which may then be used by the program code associated with contract 156 to implement the contract. The conventional implementation suffers from several drawbacks. First, in conventional implementations, the program code associated with contract 156 may be tied to an entity (e.g. entity A 163) and therefore may not be used to implement other related contracts with other entities (e.g. not involving entity A).

Further, in conventional systems, program code associated with a contract is specific to the two entities associated with the contract. Thus, if another entity such as Entity C 167 is to be associated with the contract 156, then, in conventional systems, additional code associated with: (a) Addendum 1 152 (to reflect interactions between Entity A 163 and Entity C 167 (and (b) Addendum 2 154 (to reflect interactions between Entity B 165 and Entity D 169) is typically added to involve Entity C 167. Thus, as the number of entities associated with a contract increases, the complexity of system increases dramatically thereby increasing contract administration costs (coding costs, maintenance costs, etc.) while also increasing the likelihood of errors, and making contract changes difficult or impractical to implement. Moreover, because information is shared extraneously between the entities, the potential for errors and/or data inconsistency greatly increases. In addition, in many conventional systems where a contract is used with multiple instances of entities (e.g. hundreds of patients associated with an HCP being treated for some condition), the contract is often duplicated across the instances. Thus, changes to the contract (e.g. indicating approval of a new drug to treat the condition) may not be easy and may take a long time to propagate through the system thereby limiting the utility of the platform. In the situations above, manual approvals or manual intervention is often the norm, thereby negating the advantages of the contract administration platform. While the use of blockchains to store health related information can facilitate ensuring the integrity and authenticity of the stored information, conventional techniques do not address issues of information compartmentalization, complexity, or ensure that different entities have a coherent and consistent view of stored transactions to facilitate interoperability.

Disclosed embodiments facilitate healthcare system security while promoting healthcare system integrity and interoperability. Some disclosed techniques facilitate timely exchange (e.g. at the time of a transaction) of appropriate data (e.g. compliant with legal, privacy, and business guidelines) to appropriate entities (e.g. authorized entities associated with a transaction), while facilitating a consistent and coherent view of the information across healthcare marketplace entities. Interoperability is facilitated in part because multiple entities associated with a transaction may be able tie information shared during the transaction to the transaction using an agreed upon reference. Consistency and coherency are facilitated because locally recorded data may correspond to reference data and each entity's view of the reference data (or portions of the reference data viewable by the entity) is consistent with another authorized entity's view of the data. In some embodiments, the reference data may be based on and/or take the form of a decentralized ledger. In some embodiments, the decentralized ledger may be accessible to authorized entities and each entity's view of the decentralized ledger may be compliant with legal, privacy, business, and/or contractual obligations.

In some embodiments, in response to a transaction at a first time, a first entity (e.g. a pharmaceutical provider) may receive encrypted information blocks pertaining to the transaction from one or more second entities (e.g. a healthcare provider and/or insurance provider and/or a patient). Each encrypted information block may be received from a distinct second entity and may comprise at least one sub-block that is decryptable by the first entity. The first entity (e.g. the pharmaceutical provider) may decrypt one or more of the received decryptable sub-blocks. In some embodiments, the first entity may further augment a multi-dimensional blockchain with a multi-dimensional block. The multi-dimensional block may be formed by linking at least one of the encrypted information blocks received from the one or more second entities to a current block being added to a blockchain associated with the transaction where the blockchain is maintained by the first entity. The first entity (e.g. the pharmaceutical provider) may enable access to the multi-dimensional blockchain by at least one second entity (e.g. the healthcare provider and/or insurance provider and/or a patient).

The sub-blocks decryptable by the first entity (in the received encrypted blocks) may include or point to information that may be viewed by the first entity (e.g. in compliance with legal, privacy, and/or business guidelines). Conversely, information outside the decryptable sub-blocks may not be viewable by the first entity (e.g. the pharmaceutical provider) but may be available to the second entity (e.g. the healthcare provider) that transmitted the corresponding encrypted block. Further, each encrypted block received by the first entity may: (i) be related to the transaction, and/or (ii) form part of a corresponding blockchain maintained by the second entity (e.g. the healthcare provider) that transmitted the corresponding encrypted block. In some embodiments, the current block being added to the blockchain being maintained by the first entity may also include sub-blocks, each with information decryptable by a corresponding second entity, while information outside corresponding sub-blocks may not be viewable by the second entities. The term sub-block indicates a portion of a data record or a block that is decryptable by some specific entity or entities. Accordingly, a coherent and consistent view of the transaction is available to marketplace entities while maintaining compliance with legal, privacy and/or other regulations and business considerations and promoting data integrity.

The term "blockchain" as used herein, refers to a growable list of records or "information blocks" or "blocks," where the blocks are linked using cryptographic techniques. Each block includes a cryptographic hash of the previous block, a timestamp, and transaction data. A current block being added to the blockchain is also termed the head of the blockchain. A cryptographic hash function maps data of arbitrary size to a bit string of a fixed size, which is termed a "hash." Hash functions can be deterministic (the same input will produce the same output) and may be one-way functions that are infeasible to invert (i.e. determine the original data input from the hash value). The transaction data for a block may be represented as a Merkle tree root hash. The term "Merkle tree" or "hash tree" is used to refer to a tree, where every leaf node is labeled with a hash of the transaction data and each non-leaf node is labeled with the cryptographic hash of the labels associated with its child nodes. A block header for a block to be added to the blockchain may include a hash reference to the previous block header and a hash reference to the root of the Merkle tree that contains the transaction data. Blockchains promote data integrity because alterations to data in the blockchain results in inconsistencies in one or more of the hash references. The term record or data record is also used to indicate non-final data that is to be added to a blockchain. Once a data record has been validated and finalized the data record may be added to the blockchain and form a block in the blockchain.

The term "multi-dimensional blockchain" is used to refer to a sequence of multi-dimensional records (also referred to as multi-dimensional blocks), where each multi-dimensional record includes two or more data records. In some instances, each of the data records that form a dimension of the multi-dimensional blockchain may form blocks in a distinct blockchain associated with some entity. Thus, in some embodiments, a multi-dimensional block may comprise a data record in each dimension, where the data record corresponding to a dimension may form a block in a distinct conventional blockchain associated with a corresponding entity. For example, a multi-dimensional block may include an EHR data record as one dimension, a DIR data record as another dimension, and a Transaction data record as a third dimension. Further, in some instances, the EHR data record associated with a multi-dimensional block (in the multi-dimensional blockchain) may separately form a block in a distinct EHR blockchain (i.e. distinct from the multi-dimensional blockchain). Similarly, in some instances, the DIR data record and Transaction data record associated with a multi-dimensional block may each form a block in a distinct DIR blockchain (e.g. associated with PMDP 130), and a Transaction record blockchain (e.g. associated with Payer 140), respectively. Thus, in some instances, a data record in the context of the multi-dimensional blockchain may correspond to a block in a distinct conventional blockchain. In some instances, each data record (e.g. associated with a dimension) in the multi-dimensional block may correspond to, form part of, and/or or be derived from corresponding blocks in distinct conventional blockchains. The multi-dimensional block may include a cryptographic hash of a previous multi-dimensional block, a timestamp, and data. The data for the multi-dimensional block may include hashes of the individual data records that make up the multi-dimensional block. In some embodiments, a consensus mechanism between the entities may be used to confirm correctness of data in a proposed multi-dimensional block before that multi-dimensional block is committed and locked.

Thus, the multi-dimensional block may comprise two or more encrypted data records, where each encrypted data record may be associated with a distinct entity (e.g. in the healthcare marketplace). As outlined above, the data records in a multi-dimensional block may separately form blocks in distinct blockchains, where each of the blockchains may be associated with a distinct entity. Each encrypted data record may be decrypted by the corresponding associated entity (e.g. the data record owner). Further, an encrypted data record may include portions (termed "sub-blocks") that may be (or may have been) decryptable by at least one other specific entity in addition to the encrypted data record owner. For example, the sub-block may have been decryptable by at least one other distinct entity (in addition to the data record owner) at the time the corresponding multi-dimensional block was formed. In some embodiments, at the time of multi-dimensional block formation, the sub-blocks may be separately encrypted and made available to another entity along with information to decrypt the sub-blocks. Accordingly, a multi-dimensional block may facilitate availability of transaction data to a plurality of entities associated with a healthcare marketplace, while providing a coherent and consistent view of the data to authorized marketplace entities, complying with regulations, business guidelines, and/or contractual obligations, and promoting data integrity. Entities may also ensure data correlation (e.g. of a record associated with a dimension of a multi-dimensional block in the multi-dimensional blockchain) with a corresponding block in a locally maintained blockchain. In embodiments, when information is exchanged between two entities using sub-blocks, the information exchanged via the decryptable sub-blocks may be based on an informational interface between the two entities. In some embodiments, when exchanging information (e.g. at the time of multi-dimensional block formation), each entity may encrypt blocks associated with a local blockchain maintained by the entity while generating sub-blocks that are decryptable by the other entity. The informational interface may be based on a smart contract associated with the blockchain.

The term "smart contract" is used to refer program code or logic associated with a blockchain or a blockchain platform. The "smart contract" may encode rules or agreement between two or more entities in relation to data sharing, transactions, access, contract fulfillment, etc. The smart contract may be based on a contract between two or more entities and/or agreements related to the multi-dimensional blockchain platform. For example, "smart contract" program code associated with the multi-dimensional blockchain may process transaction requests and determine the validity of transactions based on program logic.

Figure 2:
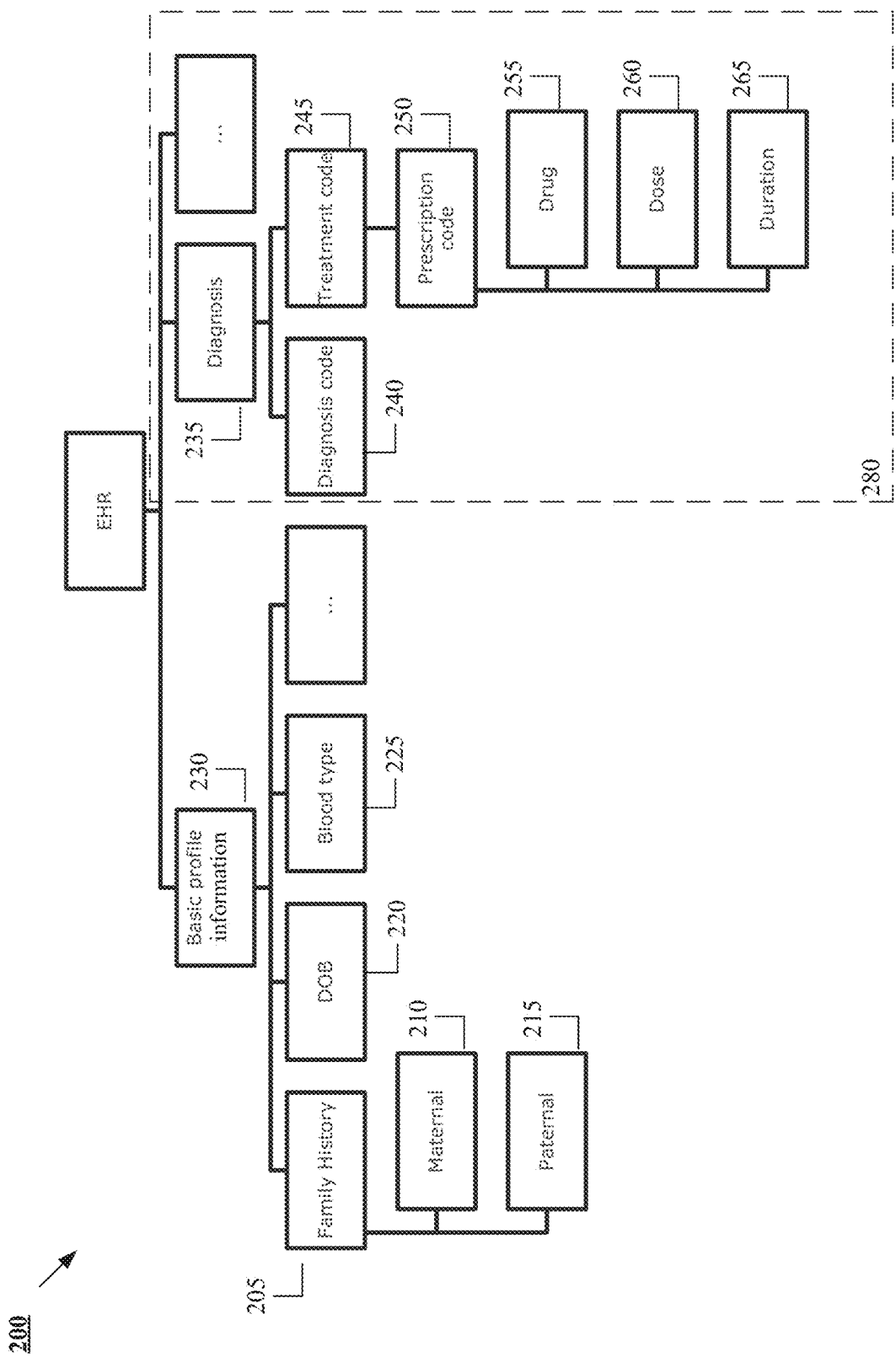
FIG. 2 shows an exemplary Electronic Health Record (EHR) illustrating some exemplary data fields in a record.

FIG. 2 shows an EHR 200 illustrating some exemplary data fields in a record. In some embodiments, EHR 200 may include information about a patient. The fields shown in EHR 200 are merely exemplary, and EHR 200 may comprise various other additional fields based on laws, standards, HCP and/or industry practice, etc. An EHR may comprise fields different from (fewer or greater than) those shown in relation to exemplary EHR 200.

For example, as shown in FIG. 2, EHR 200 may comprise basic profile information 230 about a patient, which may change relatively infrequently. Basic Profile information 230 may include Family History 205, Date of Birth (DOB) 220, Blood Type 225, etc. Family History 205 may include including Maternal History 210 and Paternal History 215. In some embodiments, EHR 200 may be created and/or maintained by HCP 120 based on information from a patient.

EHR 200 may further comprise other data fields such as Diagnosis 235 (e.g. for a current ailment), Diagnosis Code 240, which may be a standardized code for the diagnosis (such as an International Classification of Diseases (ICD) code), Treatment Code 245, which may be a standardized code to describe the treatment (e.g. such as a Current Procedural Terminology (CPT) code), Prescription Code 250 for any prescription, etc. Prescription Code 250 may further include a Drug 255 (e.g. drug name), Dosage 260 (strength and frequency), and Duration 265 (length of time over which the drug is to be taken). In some instances, EHR 200 may also comprise other fields and/or sub-fields such as an indication of whether a prescription is a new prescription, or a refill.

In some embodiments, EHR 200 for a patient may be stored as a blockchain, for example, by HCP 120 and each transaction between HCP 120 and the patient may form part of an EHR information block in the EHR blockchain. In the description below, when an EHR is maintained as a blockchain, then EHR information record 200 may also be referred to as EHR block 200. EHR block 200 may thus form a block in an EHR blockchain. When an EHR block 200 is to be added to an EHR blockchain, some of the data in EHR block 200 being added to the EHR blockchain may depend on other entities. For example, the treatment code 245 for a diagnosis may need approval and/or validation from Payer 140 (not shown in FIG. 2). As another example, a drug warning label (not shown in FIG. 2), which may form part of EHR block 200 may use input and/or approval from PMDP 130 and/or Payer 140 prior to EHR block 200 being added to the EHR blockchain.

In some embodiments, Diagnosis 235, Diagnosis Code 240, Treatment Code 245, Prescription Code 250 along with data fields Drug 255, Dosage 260, and Duration 265 may be used to form sub-block 280. Sub-block 280 is merely an example that illustrates some information that may be shared with another specific entity. In general, the information used to form sub-blocks from a data record or block in a locally maintained blockchain (e.g. an EHR blockchain) may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information). In some embodiments, data in a sub-block 280 may be shared by an entity such as HCP 120 with another healthcare marketplace entity such as Payer 140 to complete a transaction. However, patient profile information associated with Basic Profile Information 230 may be deemed private (e.g. based on legal, privacy, and/or business guidelines) and the first entity (e.g. HCP 120) may not desire to share Basic Profile Information 230, or may want to limit the portion of Basic Profile Information 230 that is shared.

Accordingly, in some embodiments, data used to form sub-block 280 may be separately encrypted. In some embodiments, encryption of data that forms sub-block 280 may be based on any appropriate cryptographic method, including symmetric key encryption techniques (where the entities, such as HCP 120 and Payer 140 share a secret key) such as Advanced Encryption Standard (AES) based techniques or variations thereof. Sub-block 280 may be encrypted (e.g. by HCP 120) prior to being shared with the other entity (e.g. Payer 140). The other entity (e.g. Payer 140) may be able to decrypt sub-block 280, for example, using the shared key.

Further, the data in EHR 200 may also be separately encrypted by HCP 120 using any secure encryption technique to form EHR block 200. For example, the data in EHR block 200 may be separately encrypted using a different key, so that it is decryptable by and available to HCP 120 but cannot be viewed by any other entity. Thus, an encrypted EHR block 200 to be added to an EHR blockchain by a first entity (e.g. HCP 120) may be encrypted prior to sharing so that: (i) a portion of the information is separately encrypted (e.g. in a sub-block 280) and is decryptable by another entity (e.g. Payer 140); and (ii) information outside of sub-block 280 cannot be decrypted or accessed by the other entity and remains private to HCP 120. Thus, in some embodiments, from an EHR data record, the data elements that may be formed may include: (a) an encrypted sub-block 280 (e.g. at the time of multi-dimensional block formation) including information in fields Diagnosis 235, Diagnosis Code 240, Treatment Code 245, Prescription Code 250, Drug 255, Dose 260, and Duration 265, which may be decryptable by some specified entity; and (b) an encrypted EHR block 200, which may include all the information in the EHR record (including EHR information present within sub-block 280 as well as EHR information from outside of sub-block 280), and is decryptable by HCP 120 (the EHR owner) but not by any other entity.

Accordingly, in some embodiments, the other entity (e.g. Payer 140) may be able to decrypt information in sub-block 280 but will not be able to decrypt encrypted information associated with EHR block 200. In some embodiments, an encrypted EHR block 200 from a first entity (e.g. HCP 120) may comprise information that may be used to form a plurality of sub-blocks, where each sub-block (e.g. sub-block 280) may be decryptable by a distinct second entity (e.g. Payer 140).

Figure 3:
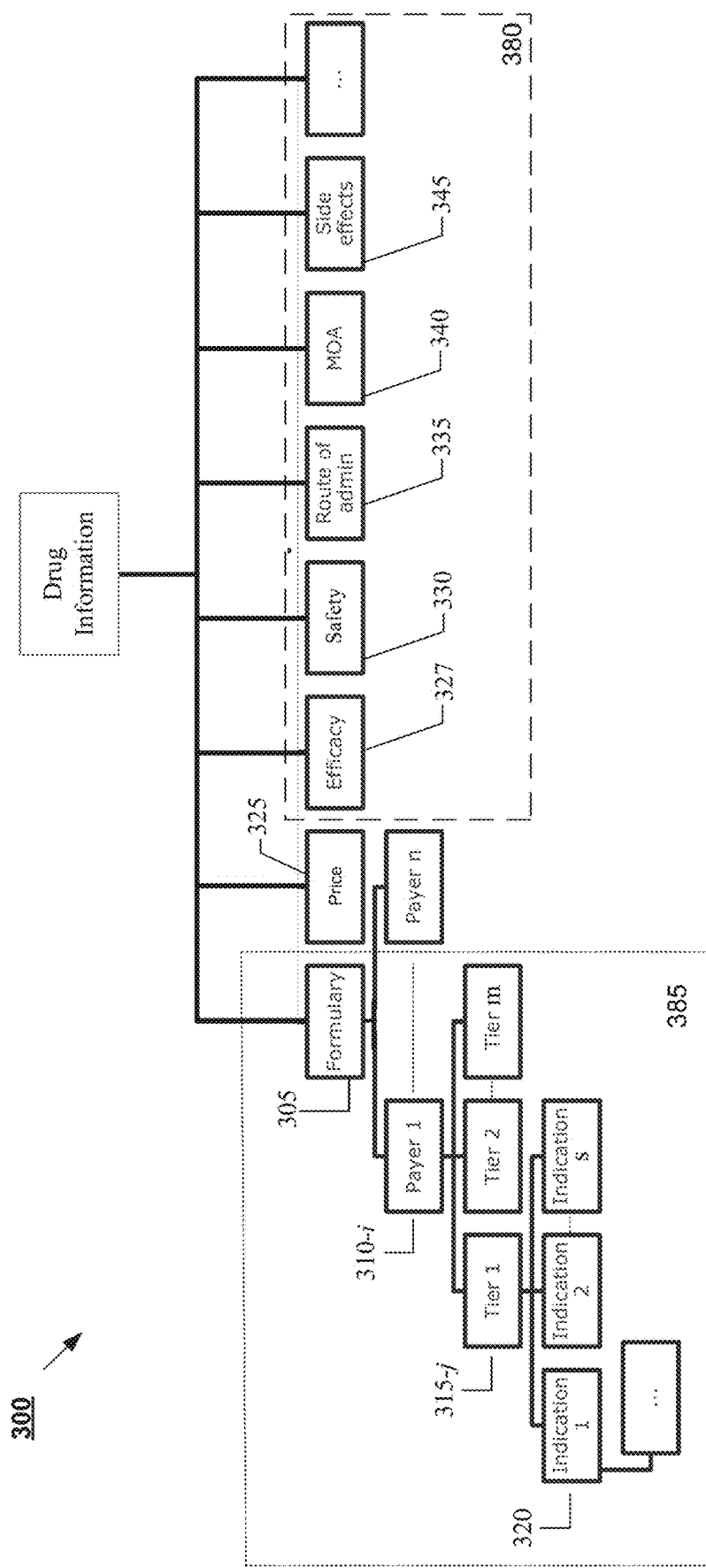
FIG. 3 shows an exemplary Drug Information Record (DIR).

FIG. 3 shows an exemplary Drug Information Record (DIR). In some embodiments, DIR 300 may include information about a drug. The fields shown in DIR 300 are merely exemplary, and DIR 300 may comprise various other fields based on laws, standards, industry practice, etc. In addition, a DIR may comprise fields different from (fewer or greater than) those shown in relation to exemplary DIR 300.

DIR 300 may comprise various data fields including Formulary 305, which may list of approved prescription drugs (e.g. generic and brand name) related to a therapeutic class. For example, a payer (such as Payer 140) for a patient may cover and/or request use of medications included in a formulary. DIR 300 may also comprise various other data fields including Price 325, which may list a price at which the drug is being made available (such as a list price or negotiated price). Formulary 305 may further include repeating Payer-i field 310-$i$, (1≤i≤n) with information about a payer. Further, each listed payer in Payer-i field 310-$i$ may include information about corresponding drug tiers in repeating Tier-j field 310-$j$, (1≤j≤m). Drug tiers list various tiers of equivalent drugs, which may depend on the formulary and payer. For example, for a formulary specified in Formulary 305 and a payer specified in Payer 1 310-1, a Tier 1 315-1 drug may be a cheaper generic drug, while a Tier 2 315-2 drug may be a more expensive generic drug, and a Tier 3 315-3 drug may be a brand name drug. Further, each Tier-j field 310-$j$ may include repeating Indication-k field 310-$k$, (1≤k≤s) with information about medical conditions for which the formulary has been approved (e.g. by a regulatory agency such as the Food and Drug Administration (FDA) and/or Payer 1 310-1) for use.

In addition, as shown in FIG. 3, DIR 300 may comprise various other fields including Efficacy 327 (which may be a measure of therapeutic effect for a medical condition), Safety 330 (e.g. drug interactions, toxicity, contraindications, etc.), Route of Administration 335 (e.g. topical, oral, intravenous, etc.), Mechanism of Action (MOA) 340 (which may identify a biochemical interaction through which a drug induces a pharmacological effect), Side Effects 345 (e.g. secondary effects), etc.

In some embodiments, DIR 300 for a patient may be stored as part of a DIR blockchain by an entity such as PMDP 130. In the description below, when a DIR is maintained as a blockchain, then DIR information record 300 may also be referred to as DIR block 300. DIR block 300 may thus form a block in a DIR blockchain. When DIR block 300 is to be added to a DIR blockchain, some of the data in a DIR information block 300 being added to the DIR blockchain may depend on validation by other entities. For example, information in formulary 305 related to a payer (e.g. payer 140) specified in Payer 1 310-1, which may form part of DIR block 300 may depend on validation by the payer (e.g. Payer 140) prior to DIR block 300 being added to the DIR blockchain.

In some embodiments, for a transaction at a point in time, information in data fields Formulary 305, Payer 1 310-1, tier information in each of the Tier-j fields 310-$j$ associated with the payer in Payer 1 310-1, information in each of the Indication-k fields 310-$k$ associated with each Tier-j field may be used to form a sub-block 385. However, information related to other payers in Payer-i fields 310-$Si$, (2≤s≤n) may not form part of sub-block 385 because the information may be confidential (e.g. between each payer in Payer-i, 2≤i≤n, and PMDP 130) and PMDP 130 may not desire to and/or may be prevented contractually from sharing information related to a payer with other payers. Sub-block 385 is merely an example that illustrates some information that may be shared with another specific entity. In general, the information used to form sub-blocks from a data record or block in a locally maintained blockchain (e.g. DIR 300) may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information).

Accordingly, in some embodiments, data in sub-block 385 may be separately encrypted. In some embodiments, encryption of data in sub-block 385 may be based on any appropriate encryption technique including symmetric key cryptography, based on a secret key shared with another entity (e.g. Payer 140, identified in Payer 1 310-1 field) prior to being shared. The other entity (e.g. Payer 140) may be able to decrypt sub-block 385, for example, based on the shared key.

In addition, as shown in FIG. 3, another sub-block 380 may be formed from DIR 300. Sub-block 380 may include fields such as Efficacy 327, Safety 330, Route of Administration 335, Mechanism of Action (MOA) 340, Side Effects 345, etc, Sub-block 380 is merely an example that illustrates some information that may be shared with another specific entity. As outlined above, the information used to form sub-block 380 from a data record or block in a locally maintained blockchain (e.g. DIR 300) may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information). Sub-block 380 may be separately encrypted using a secret key shared with another entity (e.g. PMDP 130). PMDP 130 may thus be able to decrypt and view information in sub-block 380 using the secret shared key.

Further, data in DIR block 300 may also be separately encrypted by a first entity (e.g. PMDP 130) using any secure encryption technique, so that it is decryptable by and available to the first entity (e.g. PMDP 130) but cannot be viewed by other entities (e.g. HCP 120 and/or Payer 140). Thus, in some embodiments, from a DIR data record, the data elements that may be formed may include: (a) an encrypted sub-block 385 (e.g. at the time of multi-dimensional block formation) including information in Formulary 305, Payer 1 310-1, tier information in each of the Tier-j fields 310-$j$ associated with the payer in Payer 1 310-1, and information in each of the Indication-k fields 310-$k$ associated with each Tier-j field; (b) an encrypted sub-block 380 (e.g. at the time of multi-dimensional block formation) including information in Efficacy 327, Safety 330, Route of Administration 335, Mechanism of Action (MOA) 340, Side Effects 345; and (c) encrypted DIR block 300, which may include all the information in the DIR record 300 (including DIR information also present within sub-blocks 380 and 385, as well as DIR information from outside of sub-block 380 and 385), and is decryptable by PMDP 130 (the block owner) but not by any other entity.

Thus, encrypted sub-blocks 380 and 385, which may be formed by PMDP 130, may be decryptable by HCP 120 and Payer 140, respectively. Further, PMDP 130 may encrypt DIR block 300 so that information in DIR block 300 may not be viewable by entities other than PMDP 130. In some embodiments, an encrypted DIR information block 300 from a first entity (e.g. PMDP 130) may comprise information that may be used to form a plurality of sub-blocks (e.g. 380 and 385), where each sub-block may be decryptable by a distinct second entity (e.g. HCP 120 and Payer 140, respectively).

Figure 4:
FIG. 4 shows an exemplary Health Transaction Record (HTR).

FIG. 4 shows an exemplary Health Transaction record (HTR) 400. As shown in FIG. 4, HTR 400 may comprise treatment related information and cost related information for a patient at a point in time. The fields shown in HTR 400 are merely exemplary, and HTR 400 may comprise various other fields based on laws, standards, industry practice, etc. In addition, an HTR may comprise fields different from (fewer or greater than) those shown in relation to exemplary HTR 400.

In some embodiments, HTR 400 may be maintained by entity such as Payer 140. HTR 400 may comprise various data fields including Patient 425 (e.g. a patient ID), Cost 405, which may represent a cost associated with the transaction. Cost 405 may comprise Payer cost 410 (e.g. to Payer 140), Pharmaceutical Cost 415 (e.g. cost of the prescribed drug(s)), HCP Cost (cost on account of the healthcare provider), and Patient Cost 425. Patient Cost 425 may depend on Patient Co-pay 430, Out of Pocket limits 435, and Deductibles 440, which may depend on the patient's health insurance coverage and prior transactions for the patient.

In some embodiments, HTR 400 may further comprise various other fields including Diagnosis 445 (for the patient's medical condition), Diagnosis Code 450 (e.g. for the current medical condition), Treatment Code 455 (e.g. a CPT code or another standardized code to describe the treatment), repeating field Drug Code 460-1, 460-2, . . . which may be standardized codes to identify the prescribed drugs, and Procedure Code 465 to describe medical procedures associated with treatment of the medical condition.

In some embodiments, HTR 400 for a patient at a point in time may be stored as a blockchain by an entity such as Payer 140. In the description below, when an HTR is maintained as a blockchain, then HTR information record 400 may also be referred to as HTR block 400. HTR block 400 may thus form a block in a HTR blockchain. For example, data related to a transaction between HCP 120 and a patient and/or a patient and payer 140 may form part of HTR block 400 in the HTR blockchain. When HTR block 400 is to be added to an HTR blockchain, some of the data in a HTR block 400 being added to the HTR blockchain may depend on validation by other entities. For example, information in Diagnosis 445 may be validated by HCP 120 prior to HTR block 400 being added to the HTR blockchain.

In some embodiments, for a transaction at a point in time, information in data fields Diagnosis 445, Diagnosis Code 450, Treatment Code 455, and repeating field Drug Code 460-1, 460-2, etc. may form part of a sub-block 485. Sub-block 485 may be shared with PMDP 130 to determine if a drug is approved for the stated diagnosis, to determine safety (e.g. drug interactions), etc.

In some embodiments, information in fields Patient ID 425 and co-pay 430 may be used to form another sub-block 480. Sub-block 480 may be shared with HCP 120, and may facilitate determination of co-pay information for the transaction. Sub-blocks 480 and 485 are merely examples to illustrate information that may be shared by Payer 140 with specific entities. In general, the information used to form sub-blocks from a data record or block (e.g. HTR 400) in a locally maintained blockchain may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information).

Accordingly, in some embodiments, data in sub-blocks 480 and 485 may be separately encrypted. In some embodiments, encryption of data in sub-block 485 may be based on any appropriate encryption technique including symmetric key cryptography, based on a secret key shared with PMDP 130 prior to being shared. PMDP 130 may be able to decrypt sub-block 485 based on the secret key shared between PMDP 130 and Payer 140. In addition, sub-block 480 may be separately encrypted based on a different secret key shared with HCP 120. HCP 120 may be able to decrypt and view information in sub-block 480 using the secret key shared between HCP 120 and Payer 140. Further, data in HTR information block 400 may also be separately encrypted by a first entity (e.g. Payer 140) using any secure encryption technique, so that it is decryptable by and available to Payer 140 but cannot be viewed by HCP 120 and/or PMDP 130.

Thus, in some embodiments, from an HTR data record, the data elements that may be formed may include: (a) an encrypted sub-block 480 (e.g. at the time of multi-dimensional block formation) including information in fields Patient ID 425 and co-pay 430; (b) an encrypted sub-block 485 (e.g. at the time of multi-dimensional block formation) including information in fields Diagnosis 445, Diagnosis Code 450, Treatment Code 455, and repeating field Drug Code 460-1, 460-2; and (c) encrypted HTR block 400, which may include all the information in the HTR record 400 (including HTR information also present within sub-blocks 480 and 485, as well as HTR information from outside of sub-blocks 480 and 485), and is decryptable by Payer 140 (the HTR block owner) but not by any other entity. Thus, in some embodiments, an encrypted HTR information block 400 from a first entity (e.g. Payer 140) may comprise information that may be used to form a plurality of sub-blocks (e.g. 480 and 485), where each sub-block may be decryptable by a distinct second entity (HCP 120 and PMDP 130, respectively).

Figure 5A:
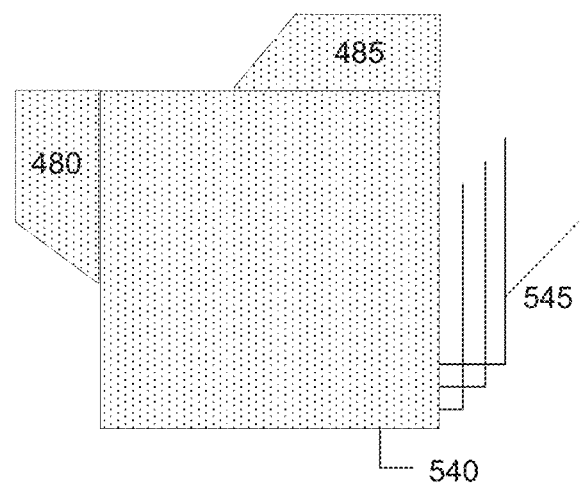
FIG. 5A shows an exemplary HTR information block comprising a plurality of sub-blocks.

FIG. 5A shows an exemplary HTR information block 540 comprising sub-blocks 480 and 485. EHR information block 540 may be added to EHR blockchain 545 maintained by a first entity such as Payer 140. In some embodiments, block 540 may be encrypted by Payer 140 so that it may be decrypted and read by Payer 140 (but not by other entities).

In some embodiments, sub-block 480 in EHR information block 540 may be encrypted by Payer 140 using symmetric key cryptography based on a secret shared key with another entity such as HCP 120. HCP 120 may decrypt sub-block 480 using the shared key. However, information in block 540 outside of sub-block 480 may not be decryptable by HCP 120.

Further, sub-block 485 in HTR information block 540 may be encrypted by Payer 140 using symmetric key cryptography based on a secret shared key with an additional entity such as PMDP 130. PMDP 130 may decrypt sub-block 485 using the shared key. However, information in block 540 outside of sub-block 485 may not be decryptable by PMDP 130.

Figure 5B:
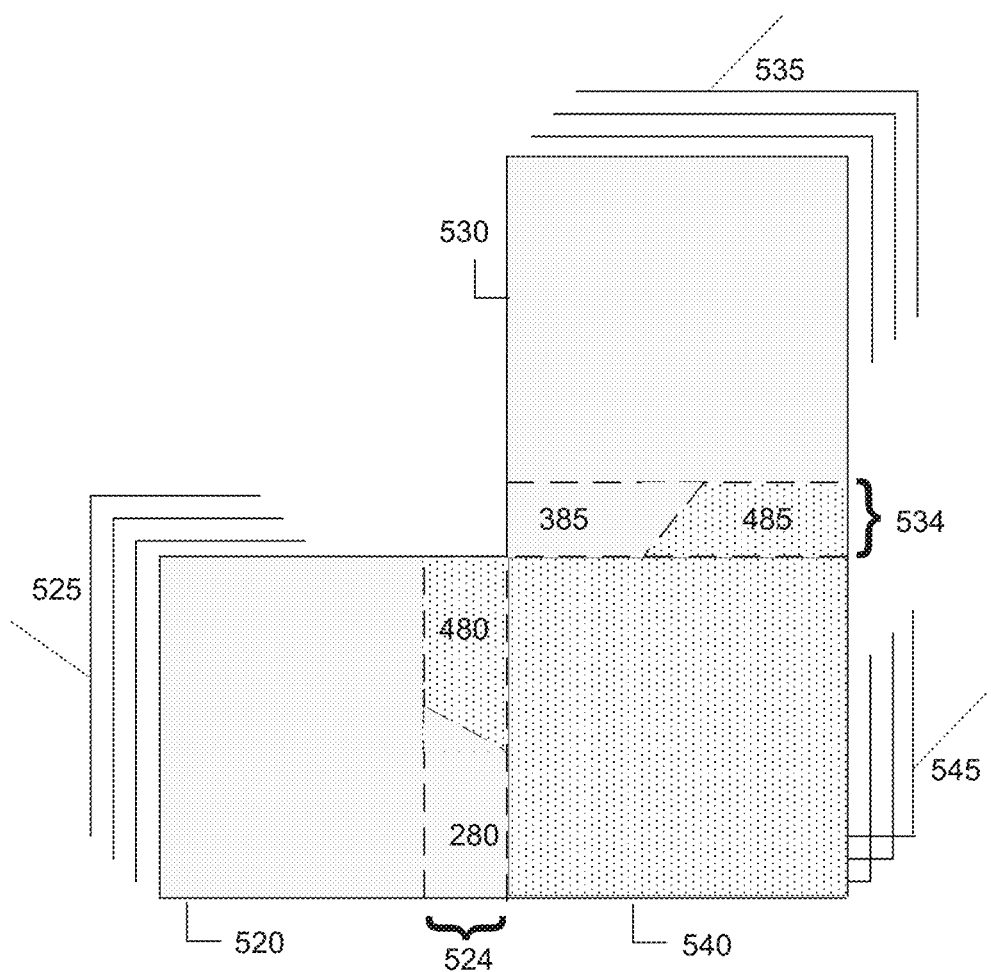
FIG. 5B shows EHR information block, DIR information block, and HTR information block depicting some sub-blocks associated with the information blocks.

FIG. 5B shows EHR information block 520, DIR information block 520, and HTR information block 540 depicting some sub-blocks associated with the information blocks.

As shown in FIG. 5B, a current information block 540 being added to HTR blockchain 545 maintained by Payer 140 may comprise information that may be used to form sub-blocks 480 and 485. As outlined above, sub-block 480 may be decryptable by HCP 120, while sub-block 485 may be decryptable by PMDP 130. As also outlined above, block 540 may be separately encrypted by Payer 140 and may not be decryptable by entities other than Payer 140 (e.g. to comply with legal, privacy, contractual, and/or business guidelines).

As shown in FIG. 5B, exemplary EHR information block 520 may comprise information that may be used to form sub-block 280. EHR information block 520 may be added to EHR blockchain 525 maintained by HCP 120. In some embodiments, sub-block 280 in EHR information block 540 may be encrypted (e.g. by HCP 120) using symmetric key cryptography based on a secret shared key with first entity Payer 140. Payer 140 may decrypt sub-block 280 using the shared key. As outlined above, HCP 120 may also decrypt sub-block 480 using the secret key shared with Payer 140. Further, information in block 520 may be separately encrypted by HCP 120 and the information may not be decryptable by entities other than HCP 120 (e.g. to comply with legal, privacy, contractual and/or business guidelines).

Further, as shown in FIG. 5B, exemplary DIR information block 530 may comprise sub-block 385. DIR information block 530 may be added to DIR blockchain 535 maintained by another second entity such as PMDP 130. In some embodiments, sub-block 385 in DIR information block 530 may be encrypted by PMDP 130 using symmetric key cryptography based on a secret shared key with Payer 140. Payer 140 may decrypt sub-block 385 using the shared key. PMDP 130 may also decrypt sub-block 485 using the secret key shared with Payer 140. Further, information in block 530 may be separately encrypted by PMDP 130 and the information may not be decryptable by entities other than PMDP 130 (e.g. to comply with legal, privacy contractual, and/or business guidelines).

In FIG. 5B, informational interface 524 between Payer 140 and HCP 120 may comprise the information shared using sub-blocks 460 and 280. Thus, information in an informational interface (e.g. informational interface 524) between two entities (HCP 120 and Payer 140) may be decrypted by both HCP 120 and Payer 140. Similarly, informational interface 534 between first entity Payer 140 and second entity PMDP 130 may comprise the information shared using sub-blocks 385 and 485, and information in informational interface 534 may be decrypted by both PMDP 130 and Payer 140.

Figure 6A:
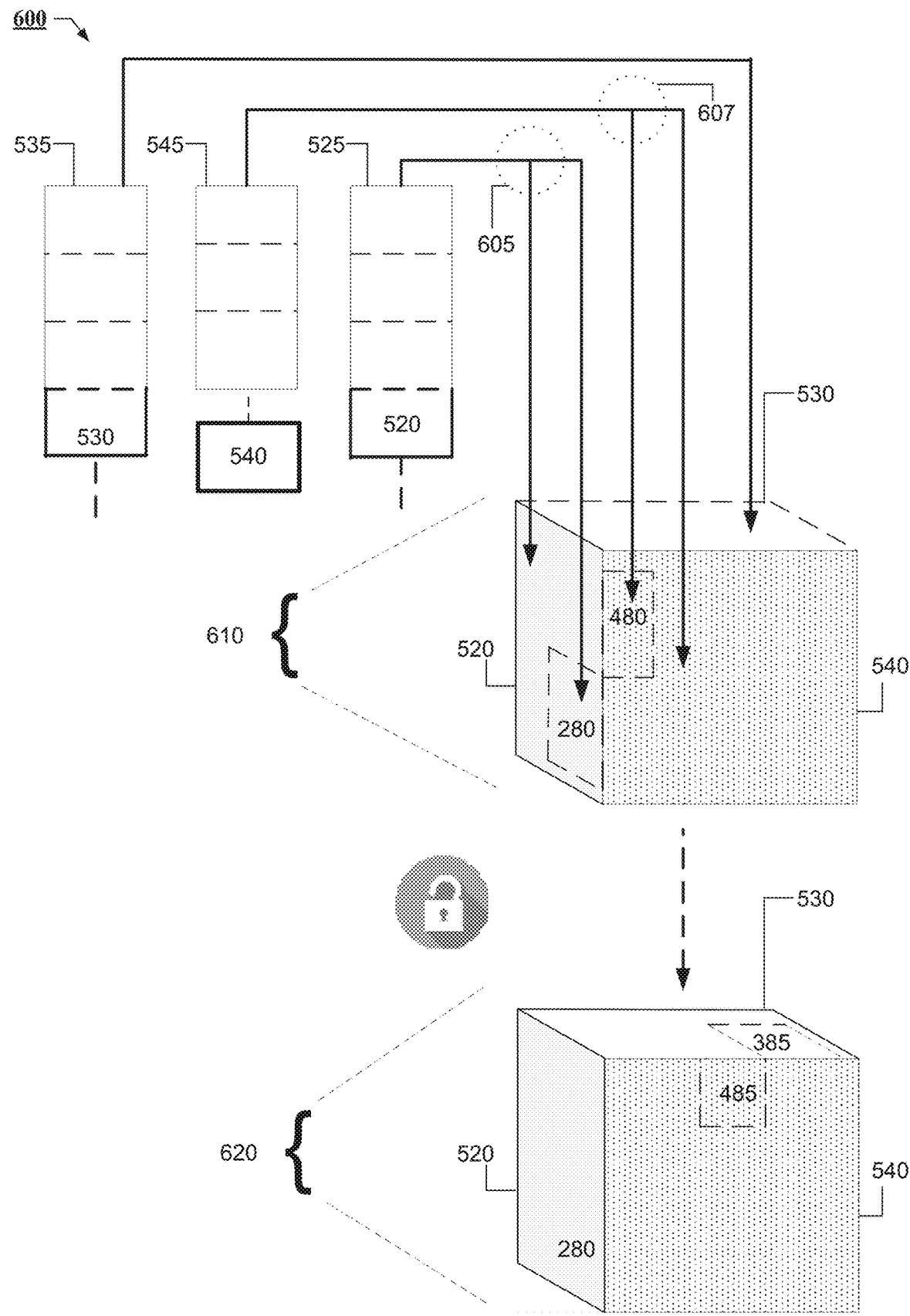
FIG. 6A shows a transaction flow associated with a multi-dimensional block.

FIG. 6A shows a transaction flow 600 associated with a multi-dimensional block. FIG. 6A is merely exemplary and, for ease of explanation, some steps between two entities in the transaction flow associated with block 540 are outlined. Additional steps to obtain a multi-dimensional block may follow a similar pattern. In FIG. 6A, the sub-blocks shown and fields described are merely examples to illustrate process flow and information that may be shared. In general, the information used to form sub-blocks from a data record or block in a locally maintained blockchain may depend on regulations (e.g. healthcare and/or privacy), laws governing information sharing (e.g. determining information that can or cannot be shared by entities), business guidelines (e.g. trade secret or sensitive information) and/or contractual obligations (e.g. between or related to the entities sharing information). When the data record has been validated and finalized, the finalized data record may be added as a block to a local blockchain FIG. 6A shows an HTR blockchain 545, which may be maintained by a first entity such as Payer 140. In FIG. 6A, data record 540 is to be added to blockchain 545. FIG. 6A also shows EHR blockchain 525 with record 520 currently at the head of the blockchain and DIR blockchain 535 with record 530 currently at the head of the blockchain. In some embodiments, blockchains 525 and 535 may be maintained by second entities HCP 120 and PMDP 130, respectively (not shown in FIG. 6A). In some embodiments, at the time the transaction request is submitted, the latest block from each blockchain may be submitted to form the multi-dimensional blockchain.

In some embodiments, updates on a traditional blockchain (e.g. one of blockchains 525, 535 or 545) by a corresponding entity (e.g. one of HCP 120, PMDP 130, or Payer 140, respectively) that includes information from another entity and/or involves other entities may be validated by one or more other entities before it is committed (e.g. locally in blockchains 525, 535, or 545 and/or in an associated multidimensional blockchain). In some embodiments, each field associated with information blocks 520, 530, and/or 540 may have a unique global field id, which may uniquely identify the field to the multi-dimensional blockchain system and/or to relevant entities, when information pertaining to that field is shared between entities.

In some embodiments, a transaction request may be sent out by an entity (e.g. by Payer 140) to relevant entities (e.g. HCP 120 and/or PMDP 130) when a record such as record 540 is to be added to a blockchain maintained by the entity. In some embodiments, the transaction request may be placed in a request pool. In some embodiments, the various entities HCP 120, PMDP 130, Payer 140 etc. may form part of a permissioned blockchain platform. In a permissioned blockchain platform, trusted entities may form a platform and invite other trusted entities to join the network. In some embodiments, the permissioned blockchain platform may also be private. In some embodiments, the permissioned blockchain platform may support multi-dimensional blockchains. Rules pertaining to access and adding blocks to the multi-dimensional blockchain, program code to determine contracts between the entities (e.g. smart contracts), validation of updates, etc. may be determined by the entities associated with the permissioned blockchain platform.

If Payer 140 is authorized to access and make updates to the platform, then, in some embodiments, when data record 540 is to be added, Payer 140 may fork and encrypt sub-block 480, which, in some instances, may comprise information from a portion of data record 540. Information in sub-block 480 may then be decrypted and read by HCP 120. In some embodiments, a symmetric encryption algorithm may be used to encrypt sub-block 480.

As outlined above, in the description below, for ease of explanation, two data records 520 and 540 are first considered from blockchains 525 and 545, respectively. As shown in FIG. 6A, forking action 605 may fork data record 540 and form forked sub-block 480. In some embodiments, forking action 605 may serve as a trigger that initiates multi-dimensional block formation. The sub-block forking action may include duplication and encryption (e.g. using a secret key shared with another entity) of some subset of data in a data record or block of a local blockchain to form a sub-block (e.g. sub-block 480). In some embodiments, the sub-block may be duplicated in memory. For example, the sub-block may reside in memory being used to form the multi-dimensional block (e.g. multi-dimensional block 610). Sub-block duplication in memory may facilitate speed, storage, and complete removal of duplicated objects (e.g. when multi-dimensional block formation has completed). Information associated with the original local block (e.g. local block 540) is not affected by the forking action (e.g. forking action 605).

For example, forking 605 may result in sub-block 480 being duplicated, split from block 480, and separately encrypted. The encryption key may be shared with HCP 120 and may take the form of an authorization code, and/or be included as part of an authorization code sent from the first entity (Payer 140) to the second entity (HCP 120) over a secure channel. HCP 120 may decrypt sub-block 480 using the authorization code received from Payer 140. In some embodiments, sub-block 480 may be duplicated in memory. Sub-block duplication in memory may facilitate speed, storage, and complete removal of duplicated objects (e.g. when multi-dimensional block formation has completed).

Further, as shown in FIG. 6A, forking action 607 may also fork data record 520 and form forked sub-block 280, when data record 520 is submitted by HCP 120. In some embodiments, forking action 607 may result in sub-block 280 being duplicated, split from data record 520, and separately encrypted. The encryption key may be shared with Payer 140 and may take the form of and/or be included as part of an authorization code sent from HCP 120 to Payer 140 over a secure channel. Payer 140 may decrypt sub-block 280 using the authorization code received from HCP 120.

In some embodiments, after validation, information in sub-blocks 280 and 480, which form the informational interface between data records 520 and 540, may be incorporated into records 520 and/or 540 (e.g. by populating and/or updating in appropriate fields in records 520 and/or 540). As an example, HCP 120 may obtain Co-pay 230 and Patient ID 425 upon decrypting and reading sub-block 480. Similarly, Payer 140 may obtain Diagnosis Code 240, Treatment Code 245, Prescription Code, etc. upon decrypting and reading sub-block 480. However, information outside of sub-block 280 in block 520 may remain private to HCP 120. Similarly, information outside of sub-block 480 in block 540 may remain private to Payer 140. As outlined earlier, the informational interface between entities may depend on laws (e.g. privacy, data sharing, healthcare, commercial, competition), contractual obligations between entities (e.g. entered into by the entities), and/or business considerations (e.g. trade secrets, etc.). Therefore, the examples above are merely illustrative and the actual data shared and/or comprised in the data records, blocks, and sub-blocks may differ from the examples.

In some embodiments, information in sub-blocks 480 and/or 280 may be validated and, after successful validation, updated data record 520 and updated data record 540 may be linked to obtain an unlocked multi-dimensional block 610. In some embodiments, updated records 520 and 540 and multi-dimensional block 610 may be retained in unlocked form (not yet committed to any blockchain) at this stage. The term "unlocked" is used to indicate that information in the multi-dimensional block 610 is not yet final and may undergo changes as the transaction moves to completion. For example, if the information in sub-blocks 480 and/or 280 is determined to be incorrect or invalid (as outlined further below), then the transaction may be rejected. In some embodiments, updated records 520 and/or 540 may be rehashed after linking. Multi-dimensional blocks (unlocked or locked) may include data and a timestamp. Data may include data records 520, 530, and/or 540. Timestamps determine the order in which multi-dimensional blocks (once validated and finalized) are linked.

In some embodiments, HCP 120 and/or Payer 140 and/or other authorized entities associated with the block chain may determine whether the information in the decrypted sub-blocks corresponds to information associated with blocks 520 and/or 540, respectively. The consensus technique may confirm the correctness of transactions that constitute the multi-dimensional block. In some embodiments, a consensus technique, such as *Byzantine* Fault Tolerance (BFT) or variations thereof such as Redundant BFT, or some other voting-based consensus technique may be used to determine if a multi-dimensional block 610 may be formed using blocks 520 and 540. When an authorized entity (e.g. Payer 140) or some specified number (e.g. a majority) of entities validates a transaction or block, then consensus is achieved.

If the transaction is confirmed as correct by the consensus technique, then a first instance of (unlocked) multi-dimensional block 610 may be formed. On the other hand, if, for example, a patient identified in Patient ID 425 in sub-block 480 does not match a Patient ID (e.g. in sub-block 280), the transaction may be deemed incorrect and the block addition request may be rejected. In some embodiments, the platform, or each entity may maintain a log of rejected transactions for traceability and debugging purposes. The log may indicate reasons or codes associated with transaction rejection.

In some embodiments, a consensus layer may include consensus techniques and may interact with a smart contracts layer to establish transaction correctness and/or validity. In some embodiments, each update on a traditional blockchain (e.g. one of blockchains 200, 300, or 400) by the corresponding entity (e.g. HCP 120, PMDP 130, or Payer 140) may be validated by smart contract program code associated with the multi-dimensional blockchain. The smart contract program code may reflect agreements between the entities in relation to data sharing, authentication, payments, etc. The smart contract layer may be viewed as an automation tool that facilitates interaction between entities without manual intervention. In some embodiments, the smart contract layer may initiate actions based on rules associated with one or more contracts when those rules have been satisfied. Each update to the multi-dimensional blockchain, and/or the passage of time, and/or other events may trigger actions by the smart contract layer.

The linking of updated records (e.g. updated record 520 and updated record 540) may be performed based on pre-defined rules agreed upon by the entities (e.g. HCP 120 and Payer 140). In some embodiments, the linking of blocks (e.g. updated block 520 and updated block 540) may be performed based on smart contract(s) associated with the multi-dimensional blockchain. After linking updated block 520 and updated blocks 540 may be rehashed. As outlined above, the links may allow an entity to correlate information in its blockchain with information in a blockchain maintained by another entity. In addition, the entities may be able to determine a transaction or transactions associated with information in a specific block maintained by that entity. Accordingly, two or more entities may have a coherent and consistent view of transactions associated with blocks in distinct blockchains.

Thus, disclosed embodiments facilitate: (a) authentication of transactions; (b) protection of transactional integrity, (c) maintain transactional provenance; (d) compliance with legal, privacy, and business guidelines when sharing information; (e) provide a context for data maintained by an organization. For example, an organization may be able to determine a source or transaction for external data received by the organization. As another example, the multi-dimensional blockchain may facilitate the use of Real World Evidence (RWE) by PDP 130 to analyze and evaluate efficacy, potency, dosage information based on actual patient prescriptions. For example, HCP may be able to share efficacy, potency, dosage information, along with some demographic information (e.g. age, location (zip code), medical condition, diagnosis, etc.) with PMDP 130 without providing any personally identifiable or sensitive information about a patient. Such RWE information has been hitherto both difficult to obtain (because of legal, privacy and other concerns) and difficult to analyze (because when obtained the information is often obtained piecemeal and devoid of context—i.e. missing demographic and/or other useful information). In some embodiments, the smart contracts layer may be used to administer the informational interfaces/data sharing so that data shared with participants may be timely, entity-specific, and compliant with laws, privacy regulations, and/or contractual obligations, while respecting business related considerations.

In FIG. 6A, updates are shown to data records that correspond to multiple dimensions of a multi-dimensional block. However, in some embodiments, a new multi-dimensional block may be formed with updates to a data record for a single dimension while substantive information associated with the other dimensions may remain unchanged. For example, drug related information associated with a drug prescribed to a patient may be updated (e.g. by PMDP 130) in a new multi-dimensional block without updates to EHR data 520 or Payer transaction record 140.

As shown in FIG. 6A, multi-dimensional block 610 may be an unlocked block, which may be non-final and may still be modified. Multi-dimensional block 610 may include links between updated data record 520 and updated data record 540. Sub-blocks 280 and 480 may form an informational interface between records 520 and 540. In some embodiments, the informational interface may be defined and/or administered by the smart contracts layer. For example, the information to be shared between entities (such as in sub-block 280 and/or sub-block 480) for a transaction type may be specified and validated by program code in a smart contracts layer associated with the multi-dimensional blockchain.

FIG. 6A shows further augmentation of multi-dimensional block 610 through a sequence of transformations, for example, by the addition of another dimension based on record 530 (which may follow the flow outlined above for multi-dimensional block 610). In FIG. 6A, at each iteration, the informational interface between two entities (two dimensions in the multi-dimensional block) is shown as being addressed. For example, in a subsequent iteration (e.g. after formation of unlocked multi-dimensional block 510), Payer 140 may fork sub-block 485 from data record 540 and PMDP 130 may fork sub-block 385 from data record 530. As outlined above, in some embodiments, sub-block 485 may be duplicated and separately encrypted with a key that may be shared with PMDP 130 (e.g. through an authorization code). Similarly, sub-block 385 may be duplicated and separately encrypted with a key that may be shared with Payer 140 (e.g. through an authorization code). After validation, blocks 530 and 540 may be linked and rehashed. Because data in further updated block 540 may have changed, the links from block 520 to newly updated block 540 may also be updated.

Figure 6B:
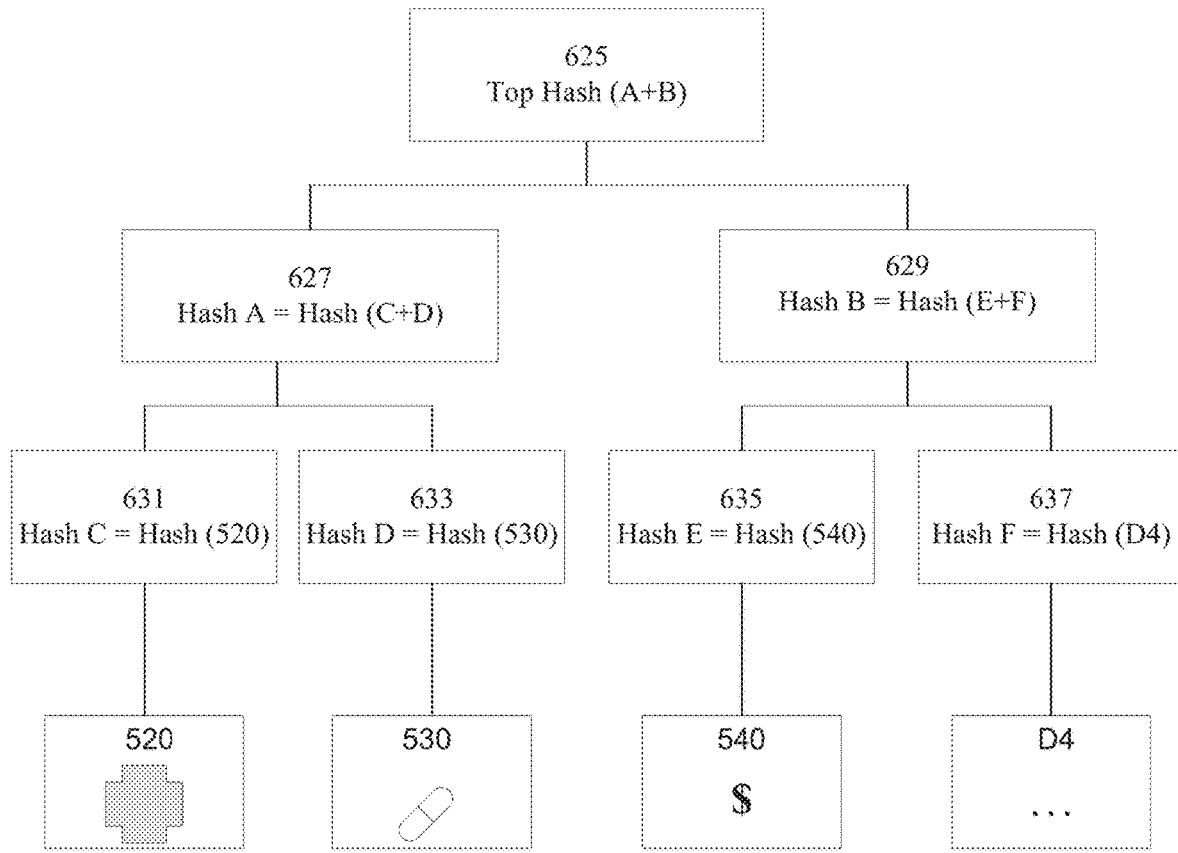
FIG. 6B shows an example Merkle tree associated with a multi-dimensional block chain that includes a plurality of data records, which may be associated with distinct individual blockchains.

FIG. 6B shows an example Merkle tree 622 associated with a multi-dimensional block chain that includes data records 520, 530, and 540. In FIG. 6B, example Merkle tree 622 is associated with a multi-dimensional block chain that includes a plurality of data records, which may each be associated with distinct individual blockchains. Merkel tree 625 is merely one example and other forms may be used as appropriate. In some embodiments, data records 520, 530, and/or 540, when validated and finalized, may form blocks in corresponding distinct blockchains (e.g. blockchains 525, 535, and/or 545, respectively). When in an unlocked state, the data in example Merkle tree 622 and records 520, 530, and 540 may not be validated and/or non-final. As shown in FIG. 6B, Hash C 631 may be obtained by using a cryptographic hash function on data record 520. Cryptographic hash functions are deterministic (produce the same output for the same input data), computationally inexpensive (in resource use to produce output for a given input), pre-image resistant (difficult to determine input from the output), and collision resistant (typically produce different outputs for different inputs). Similarly, Hash D 633, Hash E 635, Hash F 637 may be obtained by using appropriate cryptographic hash functions on data records 530, 540 and D4, respectively. In FIG. 6B, record D4 is used to illustrate some other (e.g. patient) record, but is not directly pertinent to the discussion of FIG. 6A. Cryptographic hash functions 631, 633, 635, and 639 may be specific to entities HCP 120, PMDP 130, Payer 140 and the entity associated with D4, respectively. Thus, HCP 120 may be able to decrypt data record 520 (but not PMDP 130, Payer 140, or the entity associated with D4). Conversely, data records 530, 540, and D4 may be decryptable by PMDP 130, Payer 140, and the entity associated with D4 (but not by any other entity).

Further, Hash A 627 may be obtained by using appropriate cryptographic hash functions on the combination of Hash C 631 and Hash D 633, while Hash B 629 may be obtained by using appropriate cryptographic hash functions on the combination of Hash E 635 and Hash F 637. Finally, Top Hash 625 may be obtained by using appropriate cryptographic hash functions on the combination of Hash A 627 and Hash B 629. The data associated with Hash C 631 (output of Hash (520)), Hash D 633 (output of Hash (530)), Hash E 635 (output of Hash (540)), Hash F 637 (output of Hash (D4)) may be shared (e.g. by an entity forming the multi-dimensional block) between authorized entities without compromising the security of data records 520, 530, 540 or D4. Similarly, Hash A 627, Hash B 629, and Top Hash 625 may also be shared.

Figure 6C:
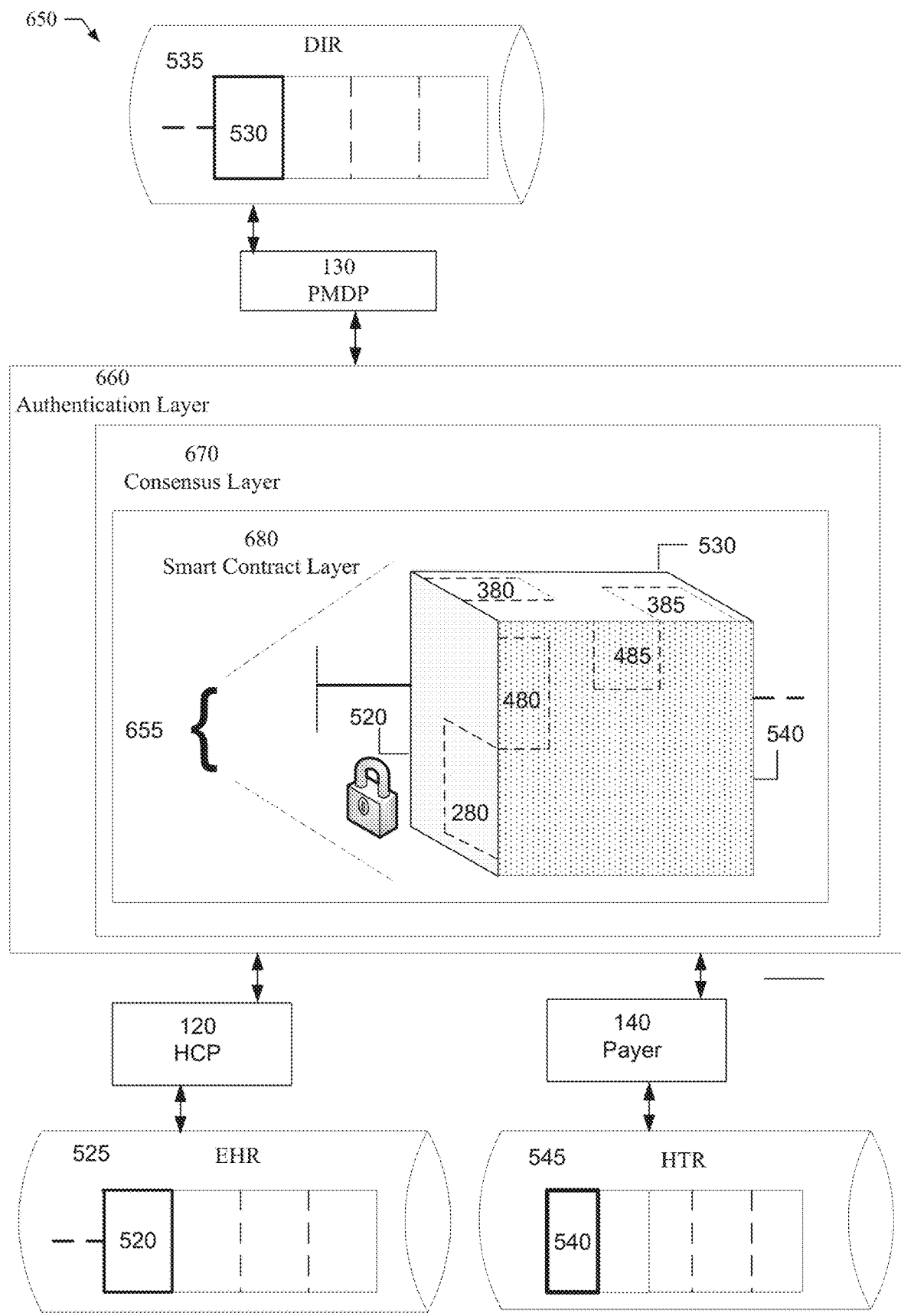
FIG. 6C shows an exemplary architecture of a system to facilitate healthcare information security and interoperability.

Referring to FIG. 6A, each iteration/step may continue with unlocked blocks. In some embodiments, when the information exchange related to the transaction is complete, and the transactions have been validated by consensus and/or the smart contract layer, blocks 520, 530 and/or 540 may be rehashed (as appropriate), links updated, and locked, and the multidimensional dimensional block may also be locked and committed as multi-dimensional block 655 (FIG. 6C). Thus, entities may be able to verify the integrity of a multi-dimensional block (e.g. a finalized multi-dimensional block 655 in FIG. 6C) associated with local blocks (e.g. finalized blocks 520, 530, and 540) associated with conventional local blockchains (e.g. blockchains 525, 525, and 545). As shown in FIG. 6C, multi-dimensional block 655 may include validated and finalized data records 520, 530 and 540, which may correspond to finalized information blocks 520, 530, and 540, respectively, in corresponding distinct local blockchains 525, 535, and 545, respectively. In some embodiments, each multi-dimensional block may include a block header with a timestamp, top hash 625, information related to the previous block, a pointer to the root of Merkle tree 625, and other appropriate information. The hash references may take the form of uniform resource locator (URL) on the private permissioned blockchain platform and/or local (entity specific) addresses.

FIG. 6C shows an exemplary architecture of a system 650 to facilitate healthcare information security and interoperability. In some embodiments, system 650 may be based on the use of multi-dimensional blockchains, which may be based on distinct blockchains maintained by the individual entities in the system. In some embodiments, system 650 may include a private permissioned blockchain platform. In some embodiments, system 650 may take the form of a cloud-based system. A cloud-based system refers to applications, services, and/or other resources (including hardware resources) that may be made available over a network (e.g. the Internet). Cloud-based systems may be based on underlying hardware and software resources and may be public (e.g. available on a fee basis to all), private (e.g. limited to an organization), or a hybrid (using some combination of public and private clouds).

Exemplary system 650 may comprise various entities. The entities may be represented by servers (hardware and/or software), which, in some instances, may be cloud based. For example, HCP 120, PMDP 130, and/or Payer 140 may include servers, and/or run on cloud-based platforms including Virtual Machines (VMs).

FIG. 6C shows an HTR blockchain 545, which may be coupled to and maintained by a first entity such as Payer 140. FIG. 6C also shows EHR blockchain 525 with block 520 at the head of the blockchain and DIR blockchain 535 with block 530 at the head of the blockchain. In some embodiments, blockchains 525 and 535 may be maintained by second entities HCP 120 and PMDP 130, respectively As shown in FIG. 6C, HCP 120, PMDP 130, and/or Payer 140 may interact with authentication layer 680. Authentication layer 660, which may include functionality for identification and management (adding, registering, and deleting) of system entities during operation. In addition, authentication layer may include functionality to validate permissions related to operations on the multi-dimensional blockchain (adding new blocks, creating links, etc.). Authentication layer 660 may interact with consensus layer 670, which may include functionality to determine the ordering of transactions and validate correctness of a set of transactions related to a block.

In some embodiments, consensus layer 670 may confirm the correctness of transactions that constitute the multi-dimensional block. In some embodiments, a consensus technique, such as Byzantine Fault Tolerance (BFT) or variations thereof such as Redundant BFT, or some other voting-based consensus technique may be used to determine if a multi-dimensional block 610 (FIG. 6A) may be formed. When a designated authoritative entity, or some specified number of entities (e.g. a majority) validates a transaction or block, consensus may be achieved in relation to validity and/or finality related to the transaction or block In some embodiments, consensus layer 670 may interact and invoke functionality in Smart Contracts layer 680 to verify correctness of an ordered set of transactions related to a block.

Smart Contracts layer 680 may comprise program code that implements logic related to a blockchain. For example, "smart contract" program code associated with the multi-dimensional blockchain may process transaction requests and determine the validity of transactions based on program logic. The logic may depend on rules agreed to by the entities for transactions related to the blockchain. For example, Smart Contracts layer 680 may reject a transaction (e.g. from HCP 120) because of incompatibility between two or more drugs prescribed to a patient. Smart contracts may operate at validation time and at commit time before a block is committed. In some embodiments, smart contracts layer 680 may determine and/or validate the informational interface between entities associated with the multi-dimensional blockchain. For example, smart contract layer 680 may encode rules or agreement between two or more entities in relation to data sharing, transactions, etc., which may be based on a real-world contract between the entities. In some embodiments, each update on a traditional blockchain (e.g. one of blockchains 625, 635, or 645) by the corresponding entity (e.g. HCP 120, PMDP 130, or Payer 140) may also be validated by smart contract layer 680 associated with the multi-dimensional blockchain. In some embodiments, the validation, finalization and linking of blocks may be performed based on smart contract(s) associated with the multi-dimensional blockchain. In some embodiments, the smart contract program code may be triggered by one or more events associated with the platform such as time, requests to add blocks from one or more entities, and/or specific requests related to a contract (e.g. identified by a contract ID), etc.

FIG. 6C shows a committed and locked multi-dimensional block 655, where information from sub-blocks 480, 280, 380, and 385 has been shared corresponding authorized relevant entities. In addition, multi-dimensional block 655 includes linkages between blocks 540, 530, and/or 520. Multi-dimensional block 655 may represent a holistic view of transaction at a point in time, in part, because it may include real world physical states associated with a drug (usage, effects, etc.), a patient (medical condition, treatment, effect), and cost at that point in time. Multi-dimensional block 655 may include links to previous block in the blockchain. Validated and finalized multi-dimensional block 655 may include finalized data records 520, 530 and 540, which may correspond to finalized information blocks 520, 530, and 540, respectively, in corresponding distinct local blockchains 525, 535, and 545, respectively.

Figure 6D:
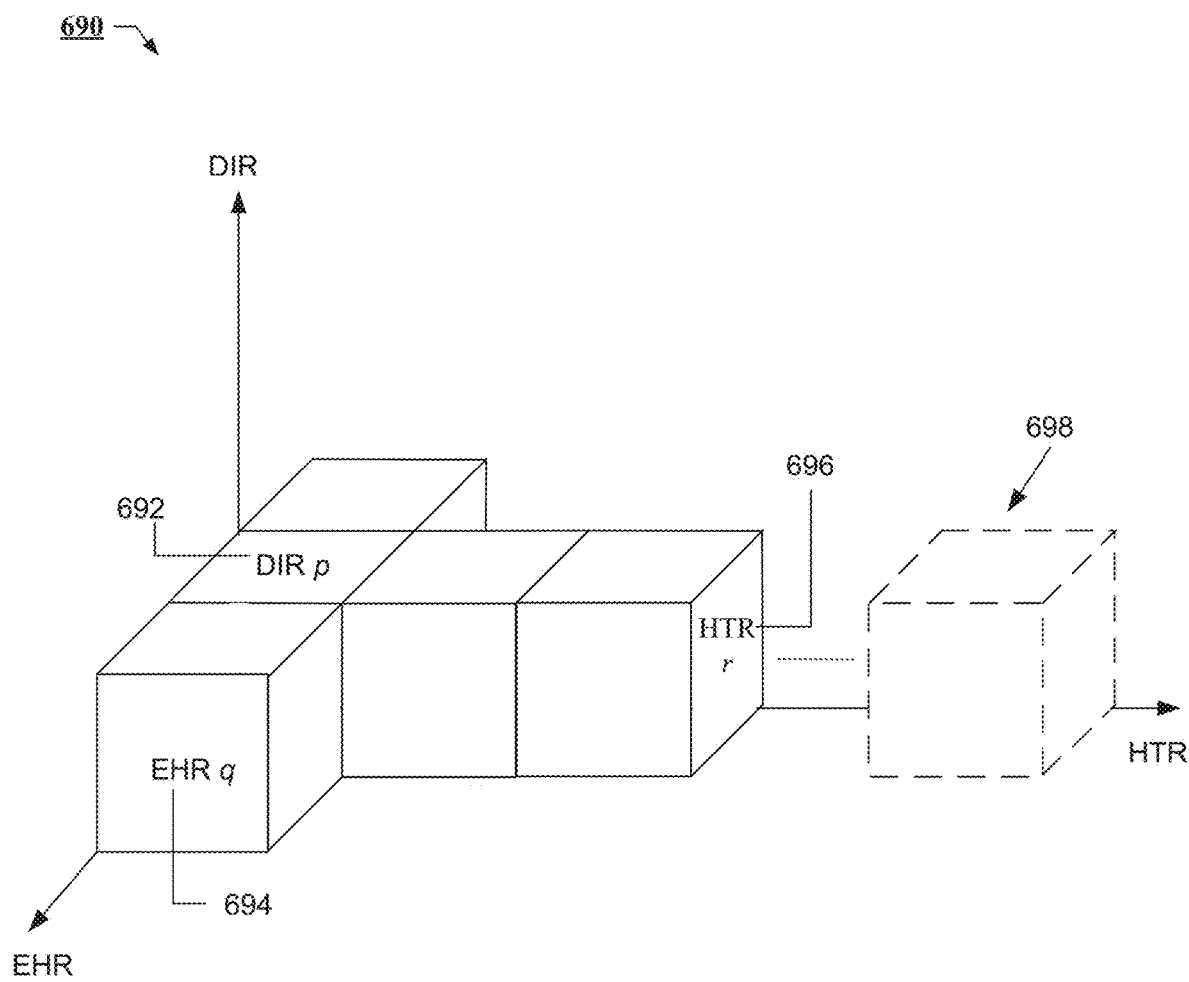
FIG. 6D is a visual depiction of multi-dimensional blocks that may be associated with an example automatic outcome based contract fulfillment.

FIG. 6D is a visual depiction of multi-dimensional blocks that may be associated with an example automatic outcome based contract fulfillment. In some embodiments, smart contract layer may facilitate automatic outcome based contracts fulfillment based on the multi-dimensional blockchain.

As shown in FIG. 6D, the 3-Dimensional (3D) blockchain 690 may comprise a sequence of 3D blocks, where each 3D block comprises an EHR data record, a DIR data record, and an HTR data record. FIG. 6C shows data record DIR p 692, which may form part of a multi-dimensional block and be associated with a specific drug (e.g. Drug p). For example, in FIG. 6D, the multi-dimensional block comprising record DIR p 692 may represent a multi-dimensional block formed when: (a) at a point in time, a patient first gets diagnosed for some specific condition, and (b) the medical provider starts treatment via a particular drug. For example, the date of treatment commencement, diagnosis code, drug fields may be shared between entities and identify the multi-dimensional block comprising record DIR p 692. As outlined above, the data shared between entities may depend on laws (e.g. privacy, data sharing, healthcare, commercial, competition), contractual obligations between entities (e.g. entered into by the entities), and/or business considerations (e.g. trade secrets, etc.). Therefore, the examples discussed here are merely illustrative and the actual data shared and/or comprised in the data records, blocks, and sub-blocks may differ from the examples.

Because a single drug (e.g. Drug p) may treat many patients, many EHR blocks including the 3D block comprising EHR q block 694 may form a multi-dimensional blockchain associated with Drug p along the EHR axis. Similarly, a single drug (e.g. Drug p) maybe associated with many transactions. Thus, many HTR blocks, including the 3D block associated with HTR r block 696 may form a multi-dimensional blockchain associated with Drug p along the HTR axis.

An outcome based contract between HCP 120 and Payer 140 may state that a payment is to be made to HCP 120 by Payer 140 when a condition is met in a committed multi-dimensional block. For example, the condition may specify one of: (i) a value for some health parameter; or (ii) an improvement in some health parameter for a patient within some time period, when the patient is treated with some drug. In some embodiments, the contract terms may be encoded as a smart contract, and the smart contract may automatically initiate payment when the condition is met as outlined further below.

When treatment for the patient commences and a prescription for the patient is submitted, a request may be sent out to the network to connect an EHR information block for the patient, a DIR information block for the prescribed drug, and a transaction information block and initiate a multi-dimensional blockchain by forming an initial multi-dimensional (3D) block (such as the 3D block comprising DIR p data record 692).

At some point in time, when a 3D block such as 3D block 698 is committed with the EHR block (associated with 3D block 698) indicating either that the value of the health parameter has been met, or that the desired improvement in the health parameter has been obtained over the course of treatment with the drug, then the smart contract may determine if the outcome was within the specified time period and automatically initiate actions. The actions may include one or more of: indicating contract completion, sending notifications to entities associated with a contract, initiating a transaction to trigger payment to HCP 120 from Payer 140, determining and/or recording parameters associated with the contract (e.g. length of time, initial and final values of relevant health parameters, number of visits, dosage, etc.). In some embodiments, the transaction to trigger payment may include the smart contract code that triggered payment to ensure trackability. The time period may be determined, for example, based on the time elapsed as determined by the difference between a timestamp associated with committed 3D block 698 at treatment end and a timestamp associated with the initial multi-dimensional block (e.g. the genesis block) when the treatment commenced in the multi-dimensional blockchain.

Referring to FIG. 6C, in some embodiments, smart contract layer 680 may also be implemented in each dimension of the multi-dimensional blockchain to ensure that multi-dimensional blocks are being built correctly. In the example above, smart contracts layer may ensure based on the EHR that each multi-dimensional block in the blockchain is related to the same patient, diagnosis and drug and/or contract ID (e.g. between HCP 120 and Payer 140).

In some embodiments, when a patient (who may an entity) in system 650 is prescribed a drug, smart contracts layer 680 may check with Payer 140 in relation to patient coverage and eligibility for the drug and may also request patient approval and agreement for the price. Upon securing agreement in relation to eligibility and price, the building of multi-dimensional block may be initiated.

In some embodiments, the holistic view enabled by a multi-dimensional blockchain may facilitate the use of machine learning and AI techniques based on RWE. For example, pharmaceutical companies and medical device providers may have very limited access to data outside of clinical trials. In some embodiments, by associating demographic information related to drug prescriptions (which may be included in an EHR sub-block in compliance with regulatory and business guidelines), pharmaceutical companies and medical device providers may be able to understand the effect of a drug on different demographic groups, change dosages, monitor adverse outcomes, etc. Such data correlation (e.g. enabled via the multi-dimensional blockchain) may enable preventive measures to be taken (e.g. lowering or increasing dosage, identifying a previously unknown drug interaction, etc.), which may decrease patient risks, increase safety and health outcomes, while also reducing cost. In addition, because of the limited sharing of information between entities, patient privacy between patients and other entities may be maintained. In addition, the use of smart contracts in conjunction with the multi-dimensional blockchain may facilitate maintenance of contract confidentiality between entities, even as payments are routed between entities.

Figure 7:
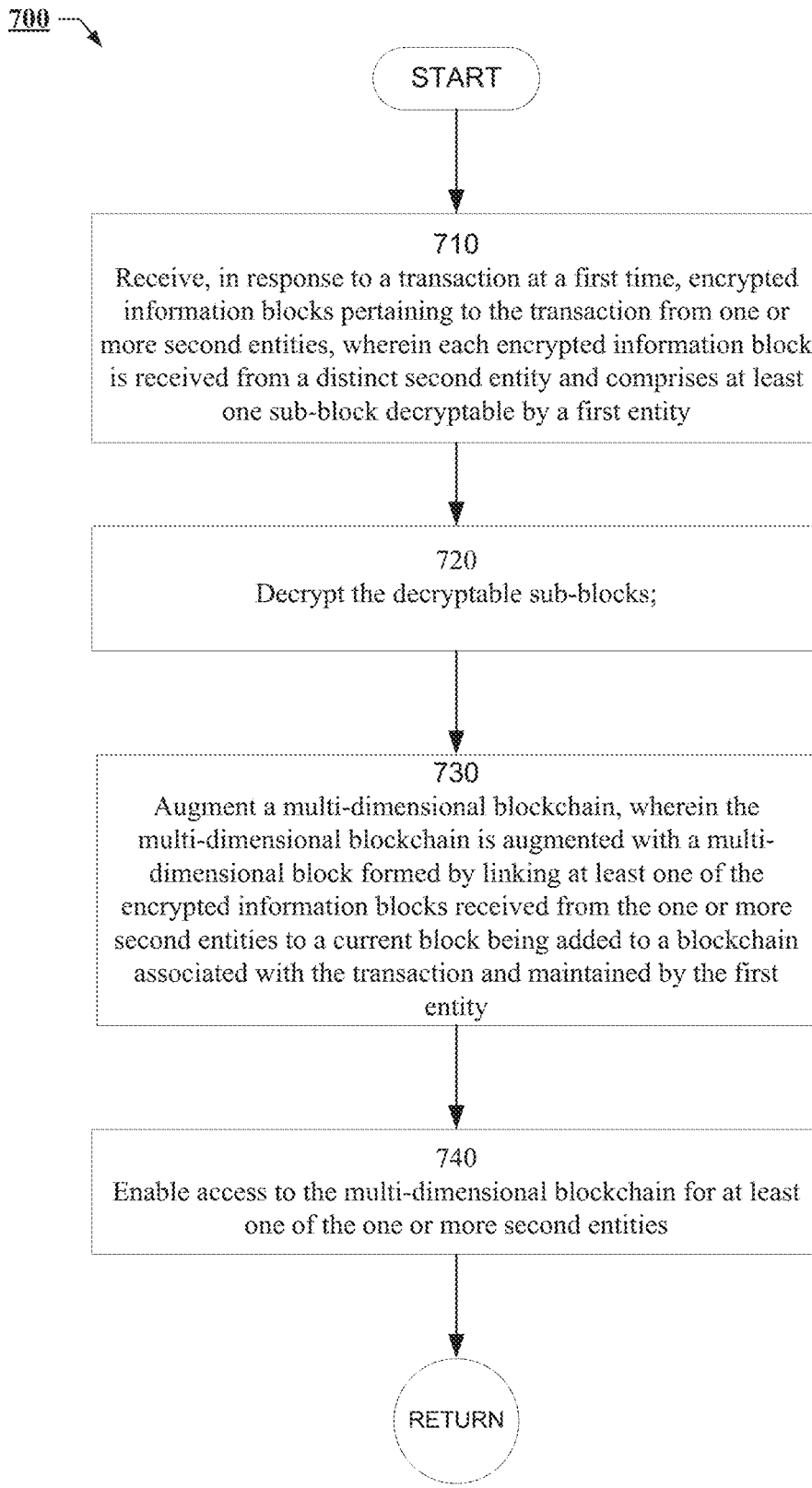
FIG. 7 shows a flowchart of an exemplary method to facilitate healthcare information security and interoperability.

FIG. 7 shows a flowchart of an exemplary method 700 to facilitate healthcare information security and interoperability. In some embodiments, method 700 may use multi-dimensional blockchains, which may be based on distinct blockchains maintained by the individual entities in a system. In some embodiments, method 7000 may run on a private permissioned blockchain platform, which, in some instances, may take the form of a cloud-based system. Method 700 may be performed by a processor, computer or networks of computers such as distributed computing systems, servers (hardware and software), including application servers, as well as cloud-based systems.

In some embodiments, method 700 may be performed at a first entity. For example, the first entity may comprise at least one server or a computer system associated with at least one of a pharmaceutical provider or a medical device provider such as PMDP 130. In some embodiments, the first entity may interact with one or more second entities. The second entities may include one or more servers or computer systems associated with healthcare providers such as HCP 120, or insurance providers such as Payer 140, or patients. In some embodiments, the first entity and the one or more second entities may form computing nodes in a distributed computing system and the multi-dimensional blockchain may form part of a permissioned private blockchain platform such as permissioned private blockchain platform 650.

In some embodiments, method 700 may be invoked when an entity such as the first entity initiates a transaction to add a block to locally maintained blockchain. The addition of the block to the local blockchain may involve inputs from one or more other entities and the permissioned private blockchain platform 650 may invoke method 700.

In some embodiments, in step 710, a first entity may receive in response to a transaction at a first time, encrypted information blocks pertaining to the transaction from one or more second entities. Each encrypted information block may be received from a distinct second entity and may comprise at least one sub block decryptable by the first entity. In some embodiments, for each encrypted information block received by the first entity, the corresponding sub-block decryptable by the first entity may be based on an informational interface between the first entity and a corresponding second entity. The informational interface between the first entity and the corresponding second entity may be determined based on predefined rules governing interaction between the first entity and the corresponding second entity. In some embodiments, the informational interface between the first entity and the corresponding second entity may be determined by a smart contract (e.g. based on smart contracts layer 680) associated with the multi-dimensional blockchain. In some embodiments, the smart contract may be associated with the multi-dimensional blockchain and form part of the permissioned private blockchain platform. In some embodiments, the smart contract may reflect agreements related to information sharing, privacy, and contractual obligations between the entities associated with the permissioned private blockchain platform.

In some embodiments, in step 720, the first entity may decrypt the sub-blocks decryptable by the first entity. In some embodiments, to decrypt the sub-blocks, the first entity may receive corresponding authorization codes from the one or more second entities associated with the received encrypted information blocks and decrypting the decryptable sub-blocks using the received authorization codes. In some embodiments, the decryption of the sub-blocks by the first entity may be based on a key shared securely with a corresponding second entity. For example, when a sub-block is encrypted by some specific second entity, the first entity may decrypt the sub-block using a key shared with or received from that second entity. In some embodiments, the shared key may be received securely by the first entity as part of an authorization code.

In step 730, the first entity may augment a multi-dimensional blockchain. The multi-dimensional blockchain may be augmented with a multi-dimensional block formed by linking at least one of the encrypted information blocks received from the one or more second entities to a current block being added to a blockchain associated with the transaction and maintained by the first entity. Augmenting may include adding a multi-dimensional block to an existing blockchain, or adding a first multi-dimensional block to a multi-dimensional blockchain structure (such as adding a multi-dimensional block to a newly created multi-dimensional blockchain). In some embodiments, the current block may comprise one or more sub-blocks, wherein each sub-block in the current block may be based on an informational interface between the first entity and a corresponding second entity and may be decryptable by the corresponding second entity. For example, the content of sub-block j in the current block may be based on an informational interface between the first entity and a corresponding second entity such as second entity j, and sub-block j may be decryptable by second entity j.

In some embodiments, augmenting may include adding a new multi-dimensional block to a multi-dimensional blockchain. The multi-dimensional blockchain may be stored and made accessible to one or more second entities associated with the permissioned private blockchain platform. In some embodiments, augmenting the multi-dimensional blockchain with a multi-dimensional block (e.g. multi-dimensional block 655) may include determining the validity of data associated with one or more sub-blocks (e.g. sub-blocks 280, 380, 385, 480, and/or 485). In some embodiments, the validity may be determined, in part, by a smart contracts layer (e.g. smart contracts layer 680) associated with the permissioned private blockchain platform. For example, the smart contracts layer (e.g. smart contracts layer 680) may request validation from one or more of the entities associated with the permissioned private blockchain platform. In some embodiments, the smart contracts layer (e.g. smart contracts layer 680) may determine an entity or entities authorized to validate the data associated with one or more sub-blocks and request validation from the authorized entity or entities. In some embodiments, validity of the data associated with one or more sub-blocks may be based on a consensus technique. In some embodiments, a Byzantine Fault Tolerance (BFT) technique may be used to determine validity and/or the reaching of consensus. In some embodiments, upon augmenting the multi-dimensional blockchain with the multi-dimensional block, the first entity may trigger at least one smart contract associated with the permissioned private blockchain platform. In some embodiments, the first entity may receive, from the smart contract based on information associated with the multi-dimensional blockchain, an indication of completion of one or more contractual milestones and/or one or more contractual outcomes between the first entity and the one or more second entities.

In some embodiments, upon augmenting the multi-dimensional blockchain with the multi-dimensional block the smart contracts layer (e.g. smart contracts layer 680) may evaluate conditions associated with contracts between entities associated with the permissioned private blockchain platform and determine whether contractual milestones (e.g. between HCP 120 and Payer 140 to determine: whether a health parameter meets some desired criteria within some time period from treatment initiation) have been satisfied, a desired contractual outcome (e.g. maintenance of the health parameter over some time period) has been met, another contract related event has occurred, etc. In some embodiments, upon determining that one or more contractual events have occurred related to some contract, the smart contracts layer (e.g. smart contracts layer 680) may perform one or more actions as outlined by contract. For example, the smart contracts layer (e.g. smart contracts layer 680) may: (a) report the contract related to event to interested authorized entities (e.g. such as the contracting parties); (b) report contract related data such as health parameters, cost metrics, and/or performance parameters (as authorized by the contract) to appropriate entities; (c) automatically initiate actions such as invoicing, approvals, payment, reporting, etc. without human intervention; (d) store information about the contract related events and associate actions taken in relation to the contract related event with the corresponding contract(s).

Further, in some embodiments, the smart contracts layer (e.g. smart contracts layer 680) may initiate other actions to analyze data and identify risk and/or other factors that may influence treatment, outcomes etc. In some embodiments, the smart contracts layer (e.g. smart contracts layer 680) may initiate or be used to initiate machine learning tools and AI techniques based on RWE associated with the multi-dimensional blockchain. For example, a specific drug (DIR) may be associated with multiple patients and each DIR data record for the drug that is associated with a multi-dimensional block in a multi-dimensional blockchain may include some non-personal demographic information (age, medical condition, zip code, other drugs being prescribed, etc.) for patients (e.g. received through an EHR sub-block) to whom the drug has been prescribed. In some embodiments, (e.g. data in the multi-dimensional blockchain has been appropriately validated using functionality associated with the smart contracts layer prior to committing a multi-dimensional block), when a designated number of transactions related to a drug has occurred and/or some designated time period has passed (e.g. from the drug's introduction or the last machine learning run), the smart contracts layer (e.g. smart contracts layer 680) may initiate machine learning based on the DIR data record associated with the drug across multiple patients. Machine learning may be able to predict or raise awareness of potential risks (medical conditions, side effects, drug interactions, etc.) associated with the drug, and/or identify instances where the drug efficacy was above par, tailor dosage, etc. Thus, pharmaceutical companies and medical device providers (e.g. PMDP 130) may be able to understand the effect of a drug on different demographic groups, change dosages, monitor adverse outcomes, etc. Such data correlation (e.g. enabled via the multi-dimensional blockchain) may enable preventive measures to be taken (e.g. lowering or increasing dosage, identifying a previously unknown drug interaction, etc.), which may decrease patient risks, increase safety and health outcomes, while also reducing cost. Moreover, in situations where DIR records associated with specific predictions can be determined, the corresponding multi-dimensional blocks (e.g. associated with those DIRs) may be used by an entity (e.g. by PMDP 130) to further validate the predictions (e.g. to determine if further study is warranted).

In step 740, the first entity may enable access to the multi-dimensional blockchain for at least one of the one or more second entities. In some embodiments, access to the multi-dimensional block may be enabled by encrypting the multi-dimensional block based on cryptographic hashing functions (e.g. as described in relation to FIG. 6B) and storing the multi-dimensional blockchain comprising the multi-dimensional block with access permissions to enable access by the one or more second entities. For example, the multi-dimensional blockchain may be stored in memory coupled to a processor or computer system performing method 700. In some embodiments, the multi-dimensional block may be stored in cloud-based storage and made accessible to appropriate entities associated with the permissioned private blockchain platform. As outlined above, while the entities associated with the permissioned private blockchain platform may be able to verify the integrity of information associated with the augmented multi-dimensional block, data records (e.g. data records 520, 530, and 540) that may be associated with specific entities may remain private to those entities. Further, as outlined above, the multi-dimensional block (e.g. multi-dimensional block 655) may include linkages between local data records data records (e.g. data records 520, 530, and 540), which, in some instances, may form blocks in corresponding distinct local blockchains (e.g. 525, 535, and 545, respectively).

Figure 8:
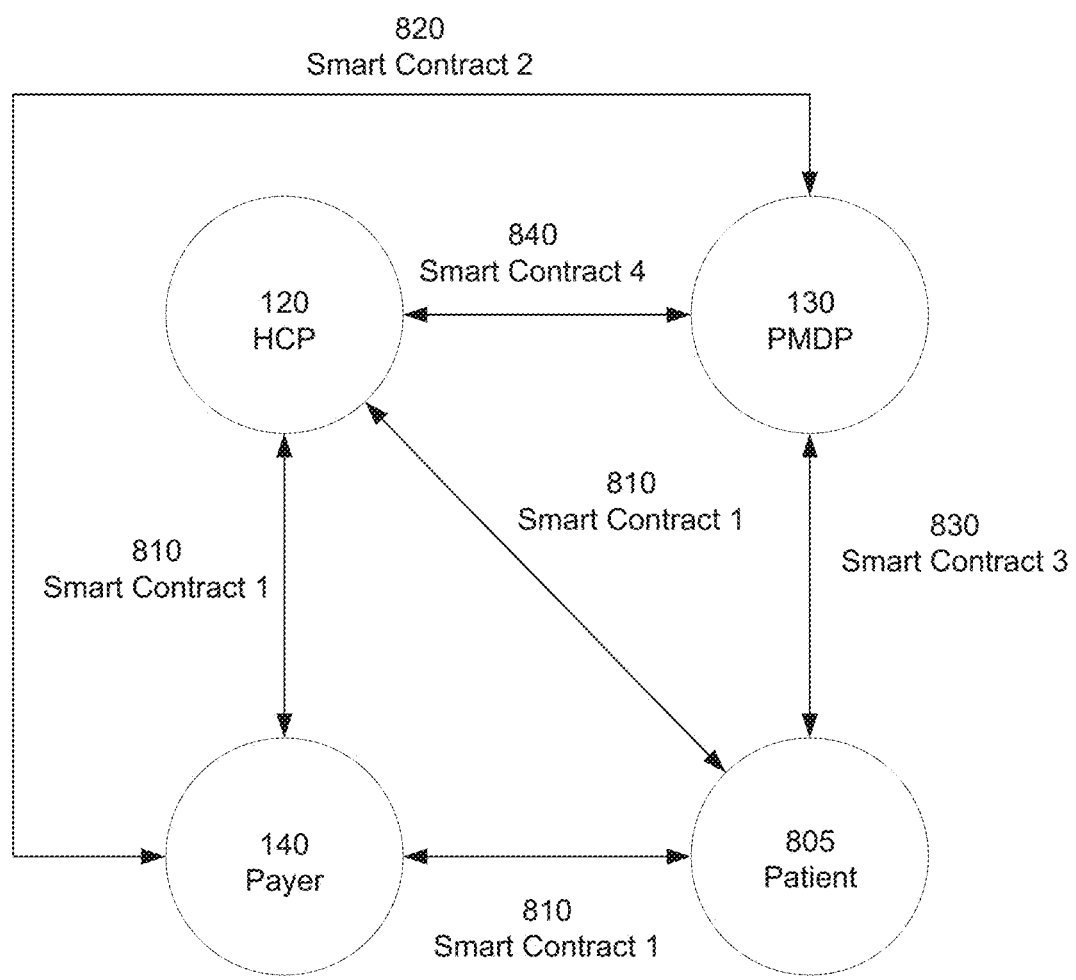
FIG. 8 shows smart contracts associated with a smart contracts layer.

FIG. 8 shows smart contracts associated with a smart contracts layer (e.g. smart contracts layer 680). As shown in FIG. 8, Smart Contract 1 810 may be implemented to reflect agreements between contracting entities Payer 140, Patient 805, and HCP 120. Smart Contract 2 820 may be implemented to reflect agreements between Payer 140 and PMDP 130. Smart Contract 3 830 may be implemented to reflect agreements between PMDP 130 and Patient 805, while Smart Contract 4 840 may be implemented to reflect agreements between PMDP 130 and HCP 120. In some embodiments, the smart contracts (e.g. Smart Contract 1 810, Smart Contract 2 820, Smart Contract 3 830, and Smart Contract 4 840) may be stored in a contract database. In some embodiments, each smart contract (e.g. Smart Contract 1 810, Smart Contract 2 820, Smart Contract 3 830, and Smart Contract 4 840) may include program code with rules to evaluate data associated with multi-dimensional blocks in a multi-dimensional blockchain. In some embodiments, the smart contracts layer (e.g. smart contracts layer 680) may decrypt information in one or more sub-blocks (on behalf of the receiving entity) and make determinations based on the code/rules associated with the corresponding smart contract. For example, the entity may delegate some functions to the smart contracts layer or the smart contracts layer may act as a proxy for the entity when authorized. In some embodiments, one or more entities may share information securely with the smart contracts layer for data validation and/or contract administration. The smart contracts layer (e.g. smart contracts layer 680) may flag data errors, ensure consistency in data reported by an entity to other entities associated with the permissioned private blockchain platform, perform data validation, specify and/or monitor the informational interface between entities and/or data sharing to ensure that authorized data is shared. For example, smart contracts layer (e.g. smart contracts layer 680) may use global field ID and/or known correlations between fields to ensure that data reported by an entity to other entities for a transaction is consistent. As one example, smart contracts layer 680 may ensure that information in a medical parameter field (e.g. blood pressure) reported by HCP 120 to patient 805 and Payer 140 is consistent.

Because of information sharing based on sub-blocks on the permissioned private blockchain platform, smart contracts layer (e.g. smart contracts layer 680) may be able to implement contracts between multiple entities such as Smart Contract 1 810 between entities Payer 140, Patient 805, and HCP 120. As outlined above, conventional systems may not be able to implement contracts between more than two entities. In addition, the multi-dimensional blockchain ensures data security for data records associated with specific entities (so that data records are not decryptable by other unauthorized entities). Moreover, because finalized data blocks (e.g. 520, 530, and 540) in the distinct local blockchains (e.g. 525, 535, and 545, respectively) correspond to the data records in finalized multi-dimensional block (e.g. multi-dimensional block 655), the entities (e.g. HCP 120, PMDP 130, and Payer 140) associated with the permissioned private blockchain platform share a consistent and coherent view of the information, which can be easily correlated with the local blockchain. The smart contracts layer (e.g. smart contracts layer 680) may also facilitate quick system updates because, when applicable, the same contract may be applied to a class of entities (e.g. patients 805). Thus, for example, an update to Smart Contract 1 810 to reflect approval of a new drug for a medical condition by Payer 140, would be quickly available to all patients associated with Smart Contract 1 (e.g. patients like patients 805 associated with Payer 140 and being treated for the medical condition by HCP 120). Further, the impact of changes to smart contracts is localized. A change to Smart Contract 4 840 between PMDP 130 and HCP 120 will affect only the entities concerned. In conventional systems, because other contracts/entities (e.g. addenda as outlined in FIG. 1B) may be tied to a contract between two entities, ripple effects may impact other entities/contracts.

In some embodiments, as outlined above, smart contracts layer (e.g. smart contracts layer 680) may evaluate contract periodically (e.g. a specified time intervals) and/or upon the occurrence of contract related events (e.g. a transaction and/or multi-dimensional block addition), request by an entity, and/or as agreed upon by the entities associated with a contract. For example, smart contracts layer 680 may evaluate conditions associated with Smart Contract 1 810 between HCP 120, Payer 140, and Patient 105. In the example above, Smart Contract 1 810 may indicate: (a) information authorized to be shared between entities (e.g. using sub-blocks); (b) specify contractual milestones (e.g. between HCP 120 and Payer 140 to determine: whether a health parameter for patient 805 meets some desired criteria within some time period from treatment initiation); (c) specify criteria for contract fulfillment; and (d) specify actions to be initiated upon contract/milestone fulfillment.

For example, a milestone in Smart Contract 1 may specify lowering of blood pressure of Patient 805 to below some range in a time period and specify a first payment to HCP 120 from Payer 140 upon meeting the milestone within some time period. Further, Smart Contract 1 may specify an additional payment to HCP 120 from Payer 140 if the blood pressure range for patient 805 stays within the specified range over some time period. Upon submission of a data record by HCP 120 (with appropriate sub-blocks decryptable by Payer 140), Smart Contract 1 may determine elapsed time from treatment initiation (e.g. based on timestamps associated with corresponding multi-dimensional blocks associated with Patient 805 and HCP 120) and check the blood pressure ranges. If the milestone has been met, Smart Contract 1 may report the milestone to entities, save information associated with the milestone, generate invoices with appropriate information, and initiate payment from Payer 140 to HCP 120. At a subsequent time, Smart Contract 1 may determine that the blood pressure range for patient 805 has stayed within the prescribed range (e.g. based on timestamps associated with corresponding multi-dimensional blocks associated with Patient 805 and HCP 120) and report the outcome to entities, save information associated with the outcome determination, generate invoices, reports, etc. with appropriate information, and initiate another payment from Payer 140 to HCP 120.

In some embodiments, upon determining that one or more contractual events have occurred related to some contract, the smart contracts layer (e.g. smart contracts layer 680) may perform one or more actions as outlined by contract. For example, the smart contracts layer (e.g. smart contracts layer 680) may: (a) report the contract related to event to interested authorized entities (e.g. such as the contracting parties); (b) report contract related data such as health parameters, cost metrics, and/or performance parameters (as authorized by the contract) to appropriate entities; (c) automatically initiate actions such as invoicing, approvals, payment, reporting, etc. without human intervention; (d) store information about the contract related events and associate actions taken in relation to the contract related event with the corresponding contract(s); and/or (e) initiate tools (e.g. machine learning etc.) to analyze data associated with the multi-dimensional blockchain.

Figure 9:
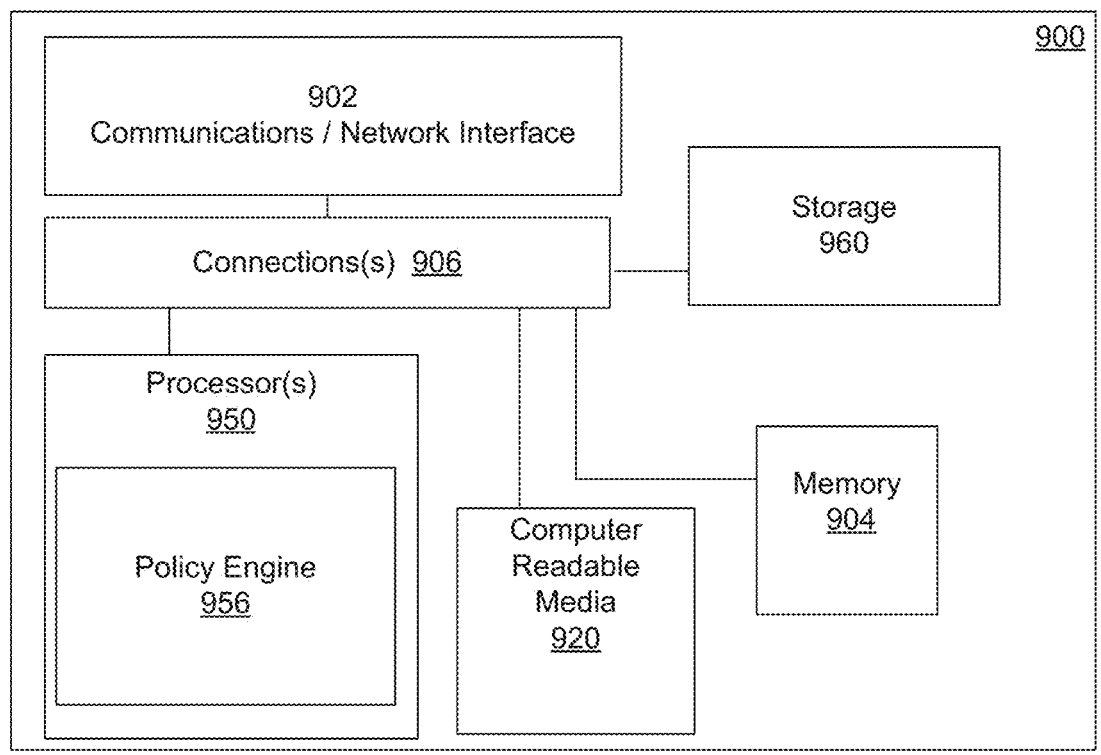
FIG. 9 shows an exemplary computer capable of facilitating healthcare system security and promoting interoperability.

FIG. 9 shows an exemplary computer 900 capable of facilitating healthcare system security and promoting interoperability. In some embodiments, computer 900 may host and/or interact with a permissioned private blockchain platform. In some embodiments, exemplary computer 900 may be a server or run servers (e.g. application servers) for one or more entities (such as HCP 120, PMDP 130, and/or Payer 140). In some embodiments, computer 900 may implement method 700 and/or other techniques disclosed herein. In some embodiments, computer 900 may form part of a distributed computing system, which may implement the permissioned private blockchain platform. In some embodiments, the distributed computing system and/or computer 900 may be cloud-based.

In some embodiments, computer 900/processor(s) 950 may be able to process transaction requests, including requests related to the addition of blocks to a blockchain, including multi-dimensional blockchains. Further, computer 900/processor(s) 950 may be able to run encryption and/or decryption algorithms, obtain hashes of information blocks, verify hashes, perform digital signing, and may be capable of executing and/or support various methods to promote security and authentication. Authentication may refer to both the verification of the integrity of stored information (e.g. in a block in a blockchain to determine any unauthorized alterations) and ensuring that entities accessing the permissioned private blockchain platform are trustworthy and have permissions to perform any requested transactions. In some embodiments, computer 900/processor(s) 950 may also augment (create or add to) blockchains with new blocks (including augmenting multi-dimensional blockchains with multi-dimensional blocks). In some embodiments, computer 900/processor(s) 950 may also store and execute smart contracts associated with blockchains to implement agreements related to privacy, information sharing, contractual execution, etc. between entities (e.g. HCP 120, PMDP 130, Payer 140, and/or patient(s)).

In some embodiments, computer 900/processor(s) 750 may be capable of analyzing and using machine learning techniques to determine relationships between various health parameters. For example, computer 900/processor(s) 950 may comprise one or more neural network processor(s), and/or distributed processors capable of being configured as a neural network, and/or be capable of executing software to model and/or simulate neural networks, which may be used to implement machine learning. For example, a PMDP 130 may use machine learning techniques based RWE information available through the multi-dimensional blocks (e.g. demographic information, side effects, drugs used in combination with a specified drug of interest, treatment outcomes etc.) to tailor usage of drug. For example, machine learning may be used to determine an effective dosage, target drugs based on demographics, improve drug interaction information, increase safety, determine the relative efficacy of various modes of administration, etc. As outlined above, this information may not be available to PMDPs 130 outside of clinical trials thereby precluding or severely limiting the use of machine learning and AI techniques.

In some embodiments, computer 900 may be coupled to other computers using communications/network interface 902, which may include wired (e.g. Ethernet including Gigabit Ethernet) and wireless interfaces. Wireless interfaces may be based on: Wireless Wide Area Network (WWAN) standards such as cellular standards including 3G, 4G, and 5G standards; IEEE 802.11x standards popularly known as Wi-Fi.

Computer 900 may include memory 904, which may include one or more of: Read Only Memory (ROM), Programmable Read Only Memory (PROM), Random Access Memory (RAM) of various types, Non-Volatile RAM, etc. Memory 904 may be implemented within processor(s) 950 or external to processor(s) 950. As used herein, the term "memory" refers to any type of long term, short term, volatile, nonvolatile, or other memory and is not to be limited to any particular type of memory or number of memories, or type of media upon which memory is stored.

Memory may comprise cache memory, primary memory, and secondary memory. Secondary memory may include computer-readable media 920. Computer-readable media may include magnetic and/or optical media, which, in some instances, may be removable media. Removable media may comprise optical disks such as compact-discs (CDs), laser discs, digital video discs (DVDs), blu-ray discs, and other optical media and further include USB drives, flash drives, solid state drives, memory cards etc. Computer 900 may further include storage 960, which may include hard drives, solid state drives (SSDs), flash memory, other non-volatile storage, and cloud-based storage.

Communications/Network interface 902, storage 960, memory 904, and computer readable media 920 may be coupled to processor(s) 950 using connections 906, which may take the form of a buses, lines, fibers, links, etc.

The methodologies described herein may be implemented by various means depending upon the application. For example, these methodologies may be implemented in hardware, firmware, software, or any combination thereof. For a hardware implementation, the processor(s) 950 may be implemented within one or more application specific integrated circuits (ASICs), digital signal processors (DSPs), neural network processors (NNPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with microcode, procedures, functions, and so on that perform the functions described herein. Any machine-readable medium tangibly embodying instructions may be used in implementing the methodologies described herein. For example, software may be stored in storage 960 and/or on removable computer-readable media. Program code may be resident on computer readable media 920, storage 960, and/or memory 904 and may be read and executed by processor(s) 950.

If implemented in firmware and/or software, the functions may also be stored as one or more instructions or code computer-readable medium 920, storage 960, and/or memory 904. Examples include computer-readable media encoded with data structures and computer programs. For example, computer-readable medium 920 may include program code stored thereon may include program code to support methods to facilitate healthcare system security and promote system interoperability, including by supporting multi-dimensional blockchains, smart contracts, consensus determination and performing other function associated with a permissioned private blockchain platform as described herein.

Processor(s) 950 may be implemented using a combination of hardware, firmware, and software. In some embodiments, computer 900 may be coupled to a display to facilitate viewing of GUIs and interaction with administrators and other users.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A processor-implemented method comprising:
   receiving, at a first entity in response to a transaction at a first time, encrypted information blocks pertaining to the transaction from one or more second entities, wherein each encrypted information block is received from a corresponding distinct second entity and comprises one or more sub-blocks decryptable by the first entity;
   decrypting, by the first entity, the one or more decryptable sub-blocks;
   augmenting, by the first entity, a multi-dimensional blockchain, wherein the multi-dimensional blockchain is augmented with a multi-dimensional block formed by linking at least one of the encrypted information blocks received from the one or more second entities to a current block being added to a blockchain maintained by the first entity, wherein the current block is associated with the transaction, wherein the multi-dimensional block comprises two or more data records, wherein at least one of the data records corresponds to the at least one encrypted information block, and wherein the at least one encrypted information block is associated with a distinct blockchain maintained by the corresponding distinct second entity; and
   enabling access to the multi-dimensional blockchain for at least one of the one or more second entities.

2. The method of claim 1, wherein, for each received encrypted information block, the one or more corresponding sub-blocks decryptable by the first entity are based on an informational interface between the first entity and the corresponding distinct second entity.

3. The method of claim 2, wherein the informational interface between the first entity and the corresponding distinct second entity is determined based on predefined rules governing interaction between the first entity and the corresponding distinct second entity.

4. The method of claim 2, wherein the informational interface between the first entity and the corresponding distinct second entity is determined by a smart contract associated with the multi-dimensional blockchain.

5. The method of claim 1, wherein enabling access to the multi-dimensional blockchain comprises:
   encrypting the multi-dimensional block based on a hashing function; and
   storing the multi-dimensional blockchain comprising the multi-dimensional block with access permissions to enable access by the one or more second entities.

6. The method of claim 1, wherein decrypting the one or more decryptable sub-blocks comprises:
   receiving, by the first entity, corresponding authorization codes from the one or more second entities associated with the received encrypted information blocks; and
   decrypting the one or more decryptable sub-blocks using the corresponding received authorization codes.

7. The method of claim 1, wherein the current block comprises one or more sub-blocks, wherein each sub-block in the current block is based on an informational interface between the first entity and a corresponding second entity and is decryptable by the corresponding second entity.

8. The method of claim 1, wherein the first entity comprises at least one server associated with at least one of a pharmaceutical provider or a medical device provider.

9. The method of claim 1, wherein the one or more second entities comprise one or more servers associated with at least one of a healthcare provider, or an insurance provider, or a patient.

10. The method of claim 1, wherein the first entity and the one or more second entities are computing nodes in a distributed computing system, and the multi-dimensional blockchain forms part of a permissioned private blockchain platform.

11. The method of claim 10, further comprising:
    triggering, by the first entity, upon augmenting the multi-dimensional blockchain with the multi-dimensional block, at least one smart contract associated with the permissioned private blockchain platform.

12. The method of claim 11, further comprising:
    receiving, from the at least one smart contract, based at least in part on information associated with the multi-dimensional blockchain, an indication of completion of one or more contractual milestones between the first entity and the one or more second entities.

13. A server for a first entity comprising:
    a memory,
    a communications interface, and
    a processor coupled to the memory and the communications interface, wherein the processor is configured to:
    receive, over the communications interface, at the first entity in response to a transaction at a first time, encrypted information blocks pertaining to the transaction from one or more second entities, wherein each encrypted information block is received from a corresponding distinct second entity and comprises one or more sub-blocks decryptable by the first entity;
    decrypt, by the first entity, the one or more decryptable sub-blocks;
    augment, by the first entity, a multi-dimensional blockchain resident in the memory, wherein the multi-dimensional blockchain is augmented with a multi-dimensional block formed by linking at least one of the encrypted information blocks received from the one or more second entities to a current block being added to a blockchain maintained by the first entity, wherein the current block is associated with the transaction, wherein the multi-dimensional block comprises two or more data records, wherein at least one of the data records corresponds to the at least one encrypted information block, and wherein the at least one encrypted information block is associated with a distinct blockchain maintained by the corresponding distinct second entity; and enable access to the multi-dimensional blockchain by at least one of the one or more second entities.

14. The server of claim 13, wherein, for each received encrypted information block, the one or more corresponding sub-blocks decryptable by the first entity are based on an informational interface between the first entity and the corresponding distinct second entity.

15. The server of claim 14, wherein the informational interface between the first entity and the corresponding distinct second entity is determined based on predefined rules governing interaction between the first entity and the corresponding distinct second entity.

16. The server of claim 14, wherein the informational interface between the first entity and the corresponding distinct second entity is determined by a smart contract associated with the multi-dimensional blockchain.

17. The server of claim 13, wherein to enable access to the multi-dimensional blockchain, the processor is configured to:
encrypt the multi-dimensional block based on a hashing function; and
store the multi-dimensional blockchain comprising the multi-dimensional block in the memory.

18. The server of claim 13, wherein to decrypt the one or more decryptable sub-blocks, the processor is configured to:
receive, by the first entity, corresponding authorization codes from the one or more second entities associated with the received encrypted information blocks; and
decrypt the one or more decryptable sub-blocks using the corresponding received authorization codes.

19. The server of claim 13, wherein the current block comprises one or more sub-blocks, wherein each sub-block in the current block is based on an informational interface between the first entity and a corresponding second entity and is decryptable by the corresponding second entity.

20. The server of claim 13, wherein the first entity comprises at least one server associated with at least one of a pharmaceutical provider or a medical device provider.

21. The server of claim 13, wherein the one or more second entities comprise one or more servers associated with at least one of a healthcare provider, or an insurance provider, or a patient.

22. The server of claim 21, wherein the first entity and the one or more second entities are computing nodes in a distributed computing system, and the multi-dimensional blockchain forms part of a permissioned private blockchain platform.

23. The server of claim 22, wherein the processor is further configured to:
trigger, upon augmenting the multi-dimensional blockchain with the multi-dimensional block, at least one smart contract associated with the permissioned private blockchain platform.

24. The server of claim 23, wherein the processor is further configured to:
receive, from the at least one smart contract, based at least in part on information associated with the multi-dimensional blockchain, an indication of completion of one or more contractual milestones between the first entity and the one or more second entities.

25. A non-transitory computer-readable medium comprising executable instructions to configure a processor to:
receive, at a first entity in response to a transaction at a first time, encrypted information blocks pertaining to the transaction from one or more second entities, wherein each encrypted information block is received from a corresponding distinct second entity and comprises one or more sub-blocks decryptable by the first entity;
decrypt, by the first entity, the one or more decryptable sub-blocks;
augment, by the first entity, a multi-dimensional blockchain, wherein the multi-dimensional blockchain is augmented with a multi-dimensional block formed by linking at least one of the encrypted information blocks received from the one or more second entities to a current block being added to a blockchain maintained by the first entity, wherein the current block is associated with the transaction, wherein the multi-dimensional block comprises two or more data records, wherein at least one of the data records corresponds to the at least one encrypted information block, and wherein the at least one encrypted information block is associated with a distinct blockchain maintained by the corresponding distinct second entity; and
enable access to the multi-dimensional blockchain by at least one of the one or more second entities.

* * * * *